(12) United States Patent
Priebe et al.

(10) Patent No.: US 9,149,489 B2
(45) Date of Patent: Oct. 6, 2015

(54) INHIBITORS OF GLYCOLYSIS USEFUL IN THE TREATMENT OF BRAIN TUMORS

(75) Inventors: Waldeman Priebe, Houston, TX (US); Charles Conrad, Spring, TX (US); Timothy Madden, Sugar Land, TX (US); Izabela Fokt, Houston, TX (US); Slawomir Szymanski, Spring, TX (US); Leposava Antonovic, Houston, TX (US)

(73) Assignee: Board of Regents, University of Texas System, Austin, TX (US)

( * ) Notice: Subject to any disclaimer, the term of this patent is extended or adjusted under 35 U.S.C. 154(b) by 202 days.

(21) Appl. No.: 12/920,104

(22) PCT Filed: Mar. 2, 2009

(86) PCT No.: PCT/US2009/035702
§ 371 (c)(1),
(2), (4) Date: Aug. 27, 2010

(87) PCT Pub. No.: WO2009/108926
PCT Pub. Date: Sep. 3, 2009

(65) Prior Publication Data
US 2011/0003758 A1 Jan. 6, 2011

Related U.S. Application Data

(63) Continuation-in-part of application No. 12/280,322, filed as application No. PCT/US2007/062789 on Feb. 26, 2007.

(60) Provisional application No. 61/032,796, filed on Feb. 29, 2008, provisional application No. 60/796,173, filed on Apr. 28, 2006, provisional application No. 60/795,621, filed on Apr. 27, 2006.

(51) Int. Cl.
*A61K 31/70* (2006.01)

(52) U.S. Cl.
CPC ..................................... *A61K 31/70* (2013.01)

(58) Field of Classification Search
None
See application file for complete search history.

(56) References Cited

U.S. PATENT DOCUMENTS

| | | | |
|---|---|---|---|
| 6,894,033 B2 | 5/2005 | Cruz et al. | |
| 6,906,048 B2 | 6/2005 | Davis et al. | |
| 6,979,675 B2 | 12/2005 | Tidmarsh | |
| 8,299,033 B2 | 10/2012 | Priebe | |
| 8,927,506 B2 | 1/2015 | Priebe | |
| 2004/0167079 A1 | 8/2004 | Tidmarsh | |
| 2007/0292478 A1 | 12/2007 | Youri | |
| 2011/0160151 A1 | 6/2011 | Priebe et al. | |
| 2012/0276108 A1 | 11/2012 | Priebe | |

FOREIGN PATENT DOCUMENTS

| WO | WO2004108166 | 12/2004 |
|---|---|---|
| WO | WO2007100728 | 10/2008 |
| WO | WO2008131024 A1 | 10/2008 |

OTHER PUBLICATIONS

Adam, M.J., Synthesis and Preliminary Evaluation of [18F]2-Deoxy-2,2-Difluoro-Glucose as a Potential PET Imaging Agent. J. Labelled Cpd. Radiopharm.42, 809-813(1999).
Adamson, J., et al., Preliminary Communication 2-Deoxy-2,2-difluoro-D-arabino-hexose ("2,2-difluoroglucose") Carbohyd. Res., 18, 345-347, 1971.
Bessell, E.M., et al., The Use of Deoxyfluoro-D-glucopyranoses and Related Compounds in a Study of Yeast Hexokinase Specificity. Biochem. J. 128, 199-204, 1972.
Finch, P. et al., The Substrate Specificity of Yeast Hexokinase: Reaction with D-Arabinose Oxime. Carbohydrate Res., 76, 225-232, 1979.
Lampidis, T.J., et al., Growth Inhibitory Effects of 2-HALO Analogs of 2-Deoxy-D-Glucose on Hypoxic Tumor Cells. Abstract Submission : 04-AB-4359-AACR, 2003.
Lampidis, T.J., et al., Efficacy of 2-Halogen Substituted D-Glucose Analogs in Blocking Glycolysis and Killing "Hypoxic Tumor Cells". Cancer Chemother Pharmacol 58, 725-734, 2006.
Aft, R.L. et al., Enhancing Targeted Radiotherapy by Copper(II) Diacetyl-bis(N4-Methylthiosemicarbazone) Using 2-Deoxy-D-Glucose1, Cancer Research 63, 5496-5504, 2003.
Mohanti, B.K., et al., Improving Cancer Radiotherapy with 2-Deoxy-D-Glucose: Phase I/II Clinical Trials on Human Cerebral Gliomas. Int. J. Radiation Oncology Biol. Phys. 35, 103-111, 1996.
McCarter, J.D., et al., Syntheses, Radiolabeling, and Kinetic Evaluation of 2-Deoxy-2-Fluoro-2-iodo-D-hexoses for Medical Imaging. Carbohydrate Res. 266(2), 273-277, 1995.
Gatenby, R.A. et al., Why do Cancers Have High Aerobic Glycolysis? Nature Reviews, 4, 891-899, Nov. 2004.
Beis I., & Newsholme E.A. The Contents Of Adenine Nucleotides, Phosphagens And Some Glycolytic Intermediates In Resting Muscles From Vertebrates And Invertebrates. Biochem J 152, 23-32. (1975).
Garber, Ken., Energy Boost: The Warburg Effect Returns in a New Theory of Cancer, Journal of the National Cancer Institute, vol. 96, No. 24, Dec. 15, 2004 at 1806.
Lu, Huasheng, et al., Hypoxia-inducible Factor 1 Activation by Aerobic Glycolysis Implicates the Warburg Effect in Carcinogenesis, J. Bio. Chem. vol. 277, No. 26, 23111 (2002).
Kurtoglu, Metin et al., Under Normoxia, 2-Deoxy-D-Glucose Elicits Cell Death In Select Tumor Types Not By Inhibition Of Glycolysis But By Interfering With N-Linked Glycosylation, Molecular Cancer Therapeutics. 6(11):3049-058, 2007.
Klionsky, D.J., et al., Autophagy as a Regulated Pathway of Cellular Degradation, Science, , 290:1717-1721. 2000.
Cuervo, A.M., Autophagy: In Sickness and in Health, Trends Cell Biol, 14: 70-77; 2004.
Shintani, T., et al., Autophagy in Health and Disease: A Double-Edged Sword, Science, 306: 990-995, 2004.
Bursch, W., et al., Programmed Cell Death (PCD). Apoptosis, Autophagic PCD, or Others? Ann. N.Y. Acad. Sci., 926: 1-12, 2000.
Ogier-Denis, E., et al., Autophagy: A Barrier or an Adaptive Response to Cancer, Biochim Biophys Acta, 1603: 113-128. 2003.

(Continued)

*Primary Examiner* — Shaojia Anna Jiang
*Assistant Examiner* — Bahar Craigo
(74) *Attorney, Agent, or Firm* — Dennis A. Bennett

(57) ABSTRACT

Provided herein are methods of treating brain tumors by administering a therapeutically effective amount of a compound of the Formulas I or II to a patient in need thereof.

1 Claim, 17 Drawing Sheets

(56) References Cited

OTHER PUBLICATIONS

Gozuacik, D., et al., Autophagy as a Cell Death and Tumor Suppressor Mechanism, Oncogene, 23: 2891-2906, 2004.

Liang, X.H., et al., Induction of Autophagy and Inhibition of Tumorigenesis by Beclin 1, Nature, 402: 672-676, 1999.

Qu, X., et al., Promotion of Tumorigenesis by Heterozygous Disruption of the Beclin 1 Autophagy Gene, J Clin Invest, 112:1809-1820. 2003.

Yue. Z., et al., Beclin 1, an Autophagy Gene Essential for Early Embryonic Development, Is a Haploinsufficient Tumor Suppressor, Proc Natl Acad Sci USA, 100: 15077-15082. 2003.

Altan, N., et al., Defective Acidification in Human Breast Tumor Cells and Implications for Chemotherapy, J Exp Med, 187: 1583-1598, 1998.

Paglin, S., et al., A Novel Response of Cancer Cells to Radiation Involves Autophagy and Formation of Acidic Vesicles, Cancer Res, 61: 439-444. 2001.

Kanzawa, T., et al., Induction of Autophagic Cell Death in Malignant Glioma Cells by Arsenic Trioxide, Cancer Res, 63: 2103-2108. 2003.

Daido, S., et al., Inhibition of the DNA-Dependent Protein Kinase Catalytic Subunit Radiosensitizes Malignant Glioma Cells by Inducing Autophagy, Cancer Res, 65:4368-4375, 2005.

Takeuchi, H., et al., Synergistic Augmentation of Rapamycin-Induced Autophagy in Malignant Glioma Cells by Phosphatidylinositol 3-Kinase/Protein Kinase B Inhibitors, Cancer Res, 65:3336-3346. 2005.

Edinger, A.L., et al. Defective Autophagy Leads to Cancer, Cancer Cell, , 4:422-424; 2003.

Kondo, Y., et al., Role of Autophagy in Cancer Development and Response to Therapy, Nat Rev Cancer, 5:726-734. 2005.

Hait, W.N., et al., A Matter of Life or Death (or Both): Understanding Autophagy in Cancer, Clin Cancer Res., Apr. 1, 12 (7 Pt 1):1961-5. 2006.

Munafo, D.B., et al., A Novel Assay to Study Autophagy: Regulation of Autophagosome Vacuole Size by Amino Acid Deprivation, J Cell Sci, 114:3619-29. 2001.

Kabeya, Y., et al., LC3, a Mammalian Homologue of Yeast Apg8p, Is Localized in Autophagosome Membranes After Processing, EMBO J, 19:5720-5728. 2000.

Mizushima, N., et al., Dissection of Autophagosome Formation Using Apg5-Deficient Mouse Embryonic Stem Cells, J Cell Biol, 152:657-668, 2001.

Masaharu, K., et al., Metabolic Pathway of 2-Deoxy-2-Fluoro-D-Glucose and 2-Deoxy-2-Fluoro-D-Mannose in Mice Bearing Sarcoma 180 Studied by Fluorine-19 Nuclear Magnetic Resonance. Chemical and Pharmaceutical Bulletin , 36(3) 1194-1197, 1988.

Bessell, E. M., et al., In Vivo and In Vitro Antitumor Effects of the Deoxyfluoro-D-Glucopyranoses. European Journal of Cancer, 9(7), 463-70, 1973.

O'Connell, T. M., et al., Identification of 2-Fluoro-2-Deoxy-D-Glucose Metabolites by 19F{1H} Hetero-RELAY. Journal of Magnetic Resonance, Series B, 109(3) 264-269, 1995.

INHIBITORS OF GLYCOLYSIS USEFUL IN THE TREATMENT OF BRAIN TUMORS

CROSS-REFERENCE TO RELATED APPLICATIONS

This application claims priority to U.S. Pat. App. Ser. No. 61/032,796 and is a continuation-in-part application of U.S. patent application Ser. No. 12/280,322, both applications are incorporated by reference herein in its entirety.

STATEMENT REGARDING FEDERALLY SPONSORED RESEARCH OR DEVELOPMENT

This invention was made with government support under CA101936 awarded by National Institute of Health. The government has certain rights in the invention.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

Reliance on glycolysis has been correlated with disease progression in cancer, and as well as a consistent and significant increase in activity of hexokinase, phosphofructokinase and pyruvate kinase. Hypoxia is also a feature of many solid cancers and has been linked to malignant transformation, metastasis and treatment resistance. Furthermore, glycolysis in cancer cells can be enhanced by certain oncogenes through the increased expression of glucose transporters and glycolytic enzymes found on tumor cells.

A serious disadvantage of treating glioblastoma is the harmful effects on normal cells and tissue. Furthermore, the mutagenic potential of certain anti-neoplastic therapies often promotes tumor resistance and can initiate other malignancies. A need exists, therefore, for cancer treatments to be developed for highly glycolytic cancer cells such as glioblastoma with little or no toxicity towards normal cells.

SUMMARY OF THE INVENTION

Compounds useful in treating brain tumors including primary tumors such as glioblastoma or high-grade gliomas, and secondary brain tumors such as metastatic brain tumors, which inhibit glycolysis are presented herein. Methods for the treatment of brain cancer in a patient comprising administering to a subject in need thereof a therapeutically effective amount of a compound of Formulas I or II as follows:

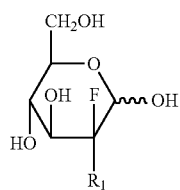

Formula I or a salt, or ester thereof, wherein:
R1 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;
R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and
R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

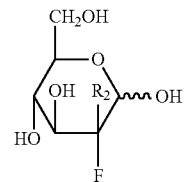

Formula II or a salt, or ester thereof, wherein:
R2 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;
R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and
R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

The compounds disclosed herein possess useful glycolysis-inhibiting activity, and may be used in the treatment or prophylaxis of a disease or condition in which glycolysis plays an active role. Thus, in the broad aspect, pharmaceutical compositions comprising one or more compounds together with a pharmaceutically acceptable carrier, as well as methods of making and using the compounds and compositions are provided.

BRIEF DESCRIPTION OF THE DRAWINGS

FIG. 10b shows U87 GBM brain tumor sensitivity in vitro to 2-DG alone and in the presence of increased concentration of D-mannose (MAN) under hypoxia. D-Mannose offers noticeable protection to U87 glioblastoma from 2-DG-mediated growth inhibition under hypoxic conditions, but this protection is significantly lower than that observed under normoxic conditions as shown in FIG. 10a.

DETAILED DESCRIPTION

Compounds useful in treating brain tumors including primary tumors such as glioblastoma (also referred to herein as "gliomas") or high-grade gliomas, and secondary brain tumors such as metastatic brain tumors, which inhibit glycolysis of the structural Formulas I and II are provided as follows:

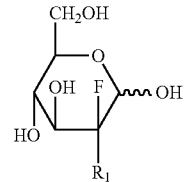

Formula I or a salt, or ester thereof, wherein:
R1 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;
R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and
R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

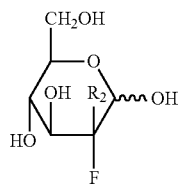

Formula II or a salt, or ester thereof, wherein:
R2 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;
R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and
R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

Figure 1:
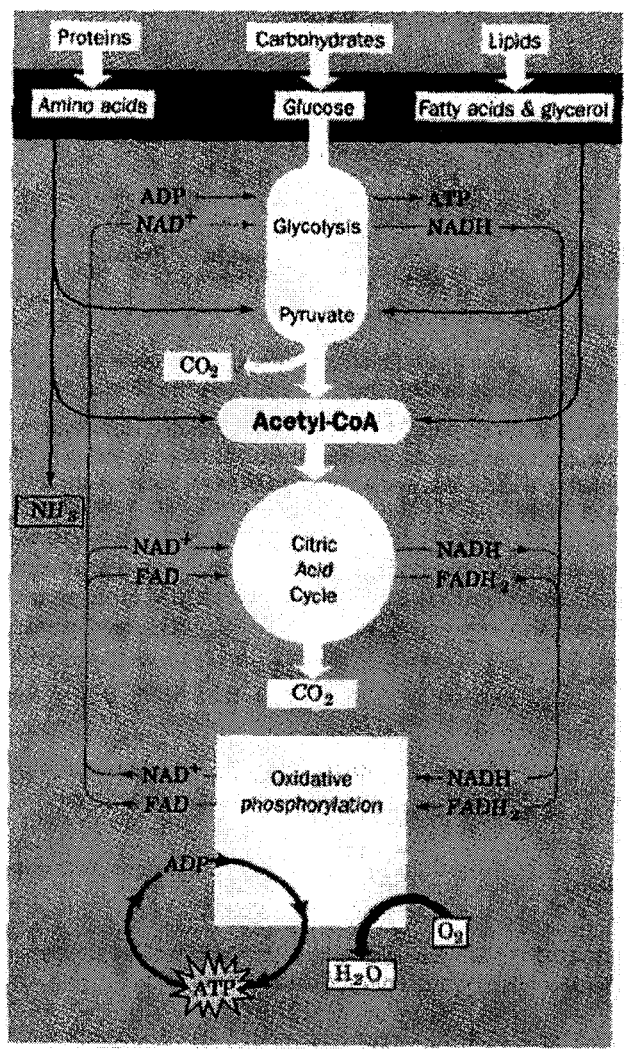
FIG. 1 shows a schematic diagram of various metabolic pathways in a eukaryotic cell.

Cells in eukaryotic organisms require energy to carry out cellular processes. Such energy is mainly stored in the phosphate bonds of adenosine 5'-triphosphate ("ATP"). As shown in FIG. 1, there are certain pathways that generate energy in eukaryotic organisms, including: (1) glycolysis; (2) the Krebs Cycle (also referred to as the TCA cycle or citric acid cycle); and (3) oxidative phosphorylation. For ATP to be synthesized, carbohydrates are first hydrolyzed into monosachamides (e.g., glucose), and lipids are hydrolyzed into fatty acids and glycerol. Likewise, proteins are hydrolyzed into amino acids. The energy in the chemical bonds of these hydrolyzed molecules are then released and harnessed by the cell to form ATP molecules through numerous catabolic pathways.

Specifically, glucose is a simple sugar or monosaccharide, and the primary source of energy for animals. Glucose is an important sugar in human metabolism having a normal concentration of about 0.1% in human blood except in persons suffering from diabetes. As a primary energy source, glucose requires no digestion.

The oxidation of glucose contributes to a series of complex biochemical reactions which provide the energy needed by cells. When oxidized (metabolized) in the body, glucose produces carbon dioxide, water and certain nitrogen compounds. Energy from glucose oxidation is used to convert ADP to adenosine 5'-triphosphate ("ATP"), a multifunctional nucleotide that is known as "molecular currency" of intracellular energy transfer.

ATP produced as an energy source during cellular respiration is consumed by different enzymes and cellular process including biosynthetic reactions, motility and cell division. For signal transduction pathways, ATP is the substrate by which kinases phosphorylate proteins and lipids and adenylate cyclase produces cyclic AMP.

ATP is an unstable molecule that tends to be hydrolyzed in water. Thus, if ATP and ADP are allowed to come into chemical equilibrium, almost all the ATP will be converted to ADP. Cells maintain ATP to ADP at a point ten orders of magnitude from equilibrium, with ATP concentrations a thousand fold higher than the concentration of ADP. This displacement from equilibrium means that the hydrolysis of ATP in the cell releases a lot of energy. Nicholls D. G. & Ferguson S. J. (2002) *Bioenergetics* Academic Press $3^{rd}$ Ed. ATP concentration inside the cell is typically 1-10 mM. Beis I., & Newsholme E. A. (1975) Biochem J 152, 23-32.

ATP is produced by redox reactions using simple sugars (e.g., glucose), complex sugars (carbohydrates), lipids and proteins. For ATP to be synthesized, carbohydrates are hydrolyzed into simple sugars such as glucose, or fats (triglycerides) are hydrolyzed to give fatty acids and glycerol. Likewise, proteins are hydrolyzed to give amino acids. Cellular respiration is the process of oxidizing these hydrolyzed molecules to carbon dioxide to generate ATP. For instance, up to 36 molecules of ATP can be produced from a single molecule of glucose. Lodish, H, et al., *Molecular Cell Biology*, $5^{th}$ Ed. New York (2004). The three main pathways to generate energy in eukaryotic organisms are: glycolysis, the Krebs Cycle (also known as the citric acid cycle), and oxidative phosphosylation.

The main source of energy for living organisms is glucose. In breaking down glucose, the energy in the glucose molecule's chemical bonds is released and can be harnessed by the cell to form ATP molecules. The process by which this occurs consists of several stages. The first is called glycolysis (the prefix glyco refers to glucose, and lysis means to split), in which the glucose molecule is broken down into two smaller molecules called pyruvic acid. As further discussed below, the next stages are different for anaerobes and aerobes.

Figure 2:
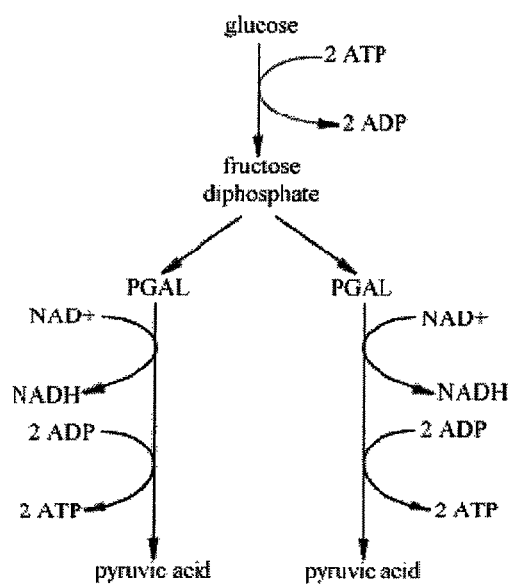
FIG. 2 shows a schematic diagram of various glycolytic pathways in a eukaryotic cell.

In glycolysis, glucose and glycerol are metabolized to pyruvate via the glycolytic pathway shown in FIG. 2. In most organisms, glycolysis occurs in the cytosol. During this process, two ATP molecules are generated. Two molecules of NADH are also produced, which can be further oxidized via the electron transport chain and result in the generation of additional ATP molecules.

Glycolysis is the first stage in the release of energy from the glucose molecule. It occurs in the cytoplasm via many enzymes. Both aerobic and anaerobic organisms use glycolysis to break down glucose to pyruvate initially. After this stage, however, aerobic organisms utilize oxygen to obtain additional energy.

Glycolysis involves the breaking down of glucose into two smaller molecules of pyruvic acid, each pyruvic acid molecule having three carbon atoms, or half of the carbons in a glucose molecule. Noteworthy, for glycolysis to occur, two ATP molecules are necessary. As shown in FIG. 2, the first ATP molecule releases a phosphate group which then joins to the glucose molecule to form glucose phosphate. Then, the second ATP molecule contributes a phosphate group, forming a molecule called fructose diphosphate. The fructose diphosphate molecule splits into two molecules of glyceraldehyde phosphate "PGAL." Each PGAL molecule then releases electrons to a coenzyme NAD+ (nicotinamide adenine dinucleotide) and phosphate groups and energy to ADP.

As a result, two NAD+ molecules become NADH, and four molecules of ADP become ATP. In addition, the two molecules of PGAL have now become molecules of pyruvic acid, which has a molecular formula of $C_3H_4O_3$. Essentially, glycolysis requires an "investment" of two ATP molecules before it can begin. Since four ATP molecules are formed as products of the reaction, there is a net gain of two ATP molecules.

At this point in anaerobic organisms, pyruvic acid (pyruvate) undergoes additional processing in order to obtain additional energy. These processes, however, are significantly less efficient than the processes which aerobes utilize: the Krebs cycle and the electron transport chain. The upregulation of glycolytic activity is an essential feature of cancers as they progress. *Energy Boost: The Warburg Effect Returns in a New Theory of Cancer*, Journal of the National Cancer Institute, Vol. 96, No. 24, Dec. 15, 2004 at 1806.

Glycolysis has been correlated with disease progression in certain cancers. For example, the Warburg effect recognizes that tumor cells rely on anaerobic glycolysis rather than on oxidative phosphorylation or the Krebs cycle (otherwise referred to as "aerobic respiration") for ATP generation, even when sufficient oxygen is available. *Hypoxia-inducible Factor 1 Activation by Aerobic Glycolysis Implicates the Warburg Effect in Carcinogenesis*, J. Bio. Chem. Vol. 277, No. 26, 23111 (2002).

Figure 3:
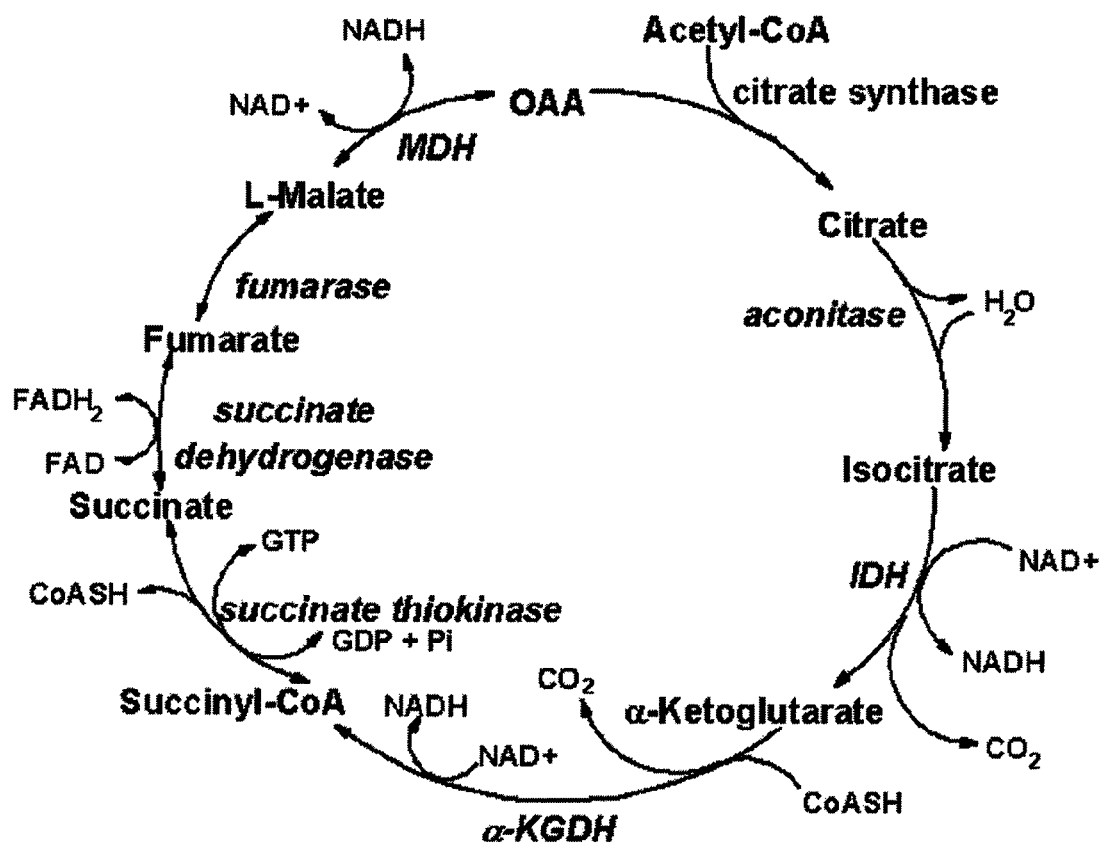
FIG. 3 shows a schematic diagram of the Krebs cycle in a eukaryotic cell.
Figure 4:
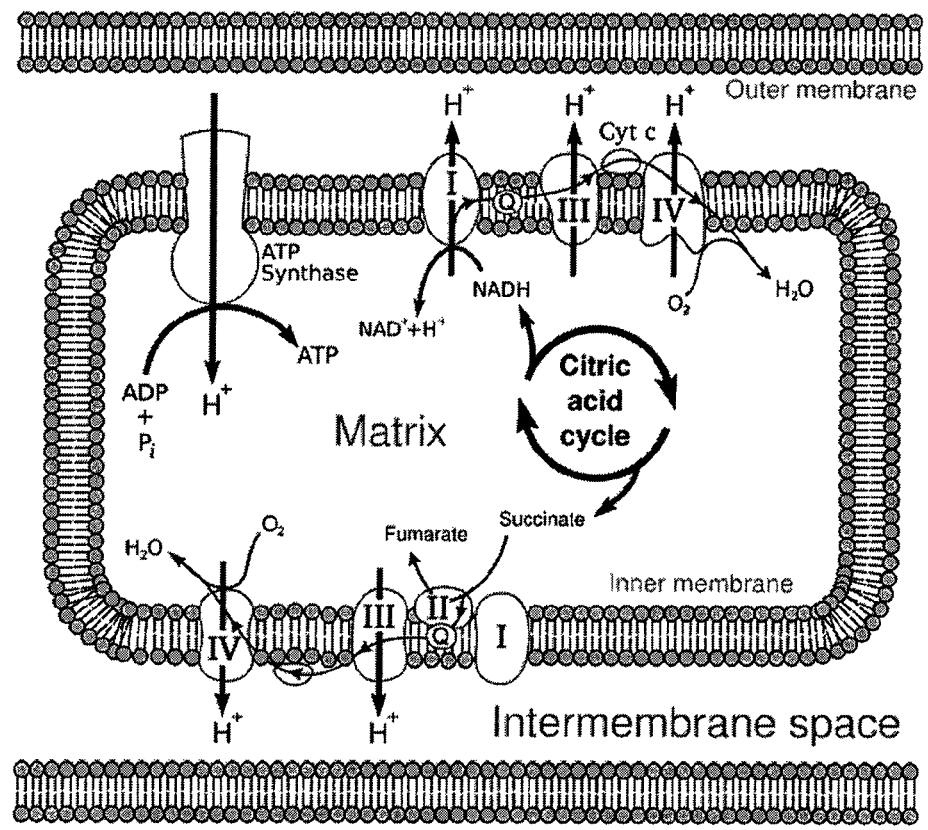
FIG. 4 shows a schematic diagram of various steps in oxidative phosphorylation in a eukaryotic cell.

As further illustrated in FIG. 2, glycolysis occurs in the cytoplasm and involves many enzyme-catalyzed steps that break down glucose (and other monosachamides) into 2 pyruvate molecules. In return, the pathway leads to the generation of a sum of 2 ATP molecules. The pyruvate molecules generated from the glycolytic pathway enter the mitochondria from the cytosol. As illustrated in FIG. 3, the molecules are then converted to acetyl co-enzyme A (Acetyl-CoA) for entry into the Krebs cycle. The Krebs cycle consists of the bonding of acetyl coenzyme-A with oxaloacetate to form citrate. The formed citrate is then broken down through a series of enzyme-catalyzed steps to generate additional ATP molecules.

Fatty acids, glycerols and amino acids can also enter the Krebs cycle after they are converted to acetyl-CoA. However, unlike glucose and other monosachamides, such molecules can by-pass the glycolytic pathway. For instance, fatty acids can be converted to acetyl-CoA through a four-step enzyme-catalyzed pathway known as β-oxidation.

Figure 5A:
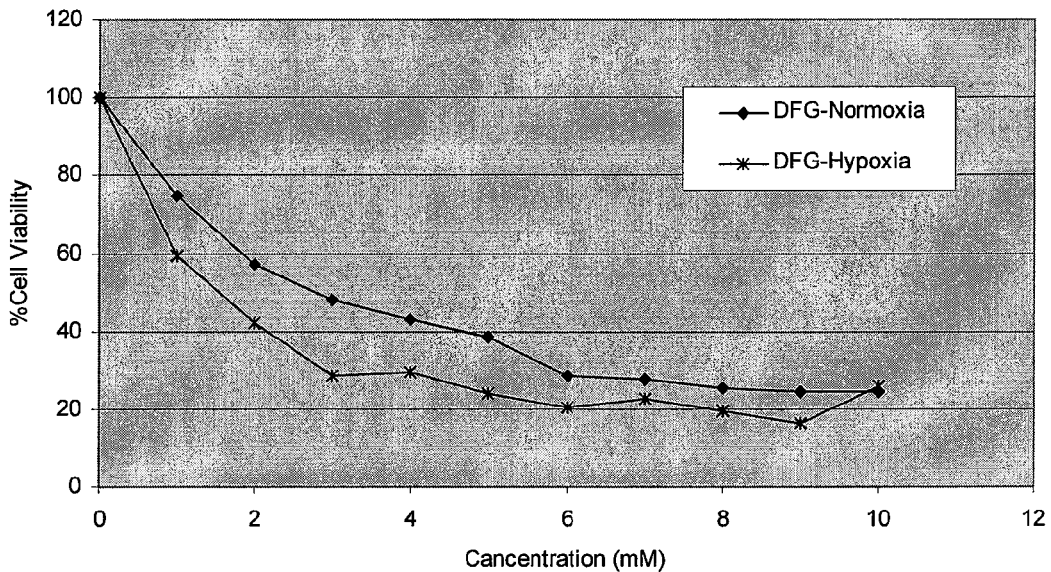
FIGS. 5a and 5b shows comparisons of DFG treatment in U87 GBM brain tumor cell line under normoxia and hypoxia performed in three independent experiments.
Figure 5B:
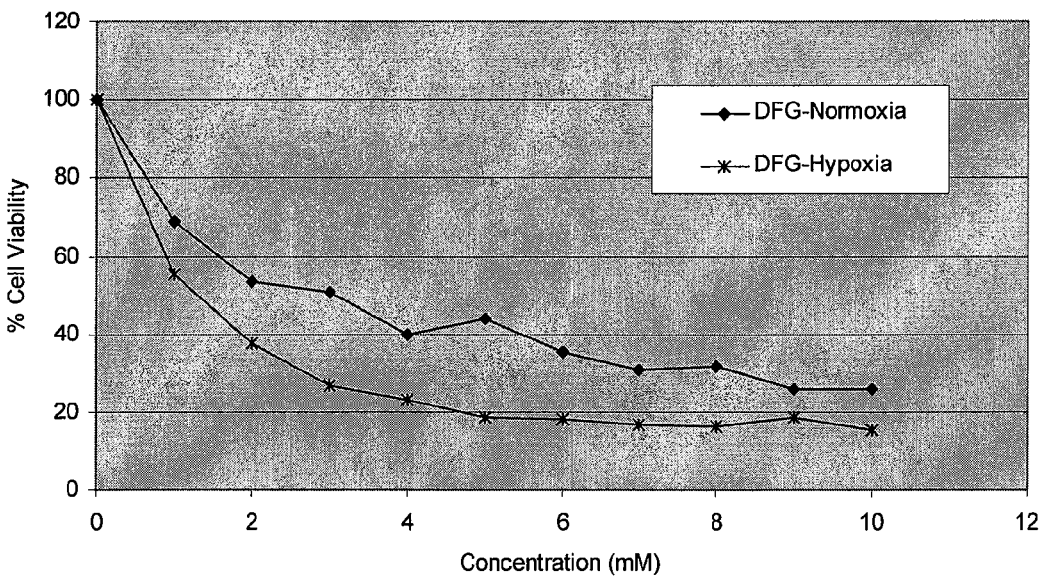

Another noteworthy metabolic pathway is ketogenesis. As illustrated in FIG. 5, ketogenesis is the process by which ketone bodies are produced as a result of fatty acid breakdown. In particular, if the amounts of acetyl-CoA generated in fatty-acid β-oxidation challenge the processing capacity of the Krebs cycle, or if the activity in the Krebs cycle is low due to low amounts of intermediates such as oxaloacetate, then acetyl-CoA is used in the biosynthesis of ketone bodies.

Ketogenesis is also associated with low carbohydrate levels in the blood. In particular, when cells are depleted of carbohydrates, as occurs during starvation or due to uncontrolled diabetes, a switch occurs from utilization of carbohydrates as the main source of energy to using fatty acid stores in the liver as a primary source of energy. Ketones produced as a result of the fatty acid oxidation serves as the main source of energy in such circumstances. Mechanisms and conditions inducing ketogenesis would include starvation and a zero carbohydrate diet (Dietary-induced Ketogenesis).

In addition to generating ATP, the catabolic processes in glycolysis and the Krebs cycle also generate electrons that become stored in the form of reduced co-enzymes, such as NADH and FADH2. As shown in FIG. 3, these co-enzymes participate in oxidative phosphorylation, where their electrons pass through an electron transport chain across the mitochondrial membrane. During this process, the protons from NADH and FADH2 enter the mitochondrial intermembrane space. Consequently, the electron transport chain leads to the formation of a proton gradient within the intermembrane space. Finally, the protons flux from the intermembrane space to the mitochondrial matrix through specific proton channels that catalyze the synthesis of additional ATP molecules.

Like normal cells, cancer cells also utilize metabolic pathways to generate ATP. However, unlike normal cells, tumor cells may rely on anaerobic glycolysis rather than other pathways for obtaining energy. Therefore, cancer cells can often lack adequate oxygen supplies for sustaining oxygen-dependent catabolic pathways. Observations by Otto Warburg show that highly proliferative tumors utilize glycolysis for cellular energy production, even in the presence of adequate amounts of oxygen (termed oxidative glycolysis or the "Warburg effect"). Under such conditions, the tumor cells up-regulate the expression of both glucose transporters and glycolytic enzymes, in turn, favoring an increased uptake of glucose (as well as their analogs) as compared to normal cells in an aerobic environment. This tumor adaptive response holds true for malignant gliomas as well.

Furthermore, many cancers such as malignant gliomas and pancreatic cancer are intrinsically resistant to conventional therapies and represent significant therapeutic challenges. Malignant gliomas have an annual incidence of 6.4 cases per 100,000 (Central Brain Tumor Registry of the United States, 2002-2003) and are the most common subtype of primary brain tumors and the deadliest human cancers. In its most aggressive manifestation, glioblastoma multiforme (GBM), the median survival duration for patients ranges from 9 to 12 months, despite maximum treatment efforts. In fact, approximately one-third of patients with GBM their tumors will continue to grow despite treatment with radiation and chemotherapy. Similarly, depending on the extent of the tumour at the time of diagnosis, the prognosis for pancreatic cancer is generally regarded as poor, with few victims still alive 5 years after diagnosis, and complete remission rare.

Further, in addition to the development of tumor resistance to treatments, another problem in treating malignant tumors is the toxicity of the treatment to normal tissues unaffected by disease. Often chemotherapy is targeted at killing rapidly-dividing cells regardless of whether those cells are normal or malignant. However, widespread cell death and the associated side effects of cancer treatments may not be necessary for tumor suppression if the growth control pathways of tumors can be disabled. For example, one approach is the use of therapy sensitization, i.e. using low dose of a standard treatment in combination with a drug that specifically targets crucial processes in the tumor cell, increasing the effects of the other drug.

Accordingly, the glycolytic pathway has become a potential target for the selective inhibition of many tumor cells, particularly glioblastomas and pancreatic cancers and other highly glycolytically sustained tumors. The inhibition of glycolysis would be selective for such tumor cells because normal cells in aerobic conditions would be able to survive such inhibition by generating energy through other pathways (e.g., the Krebs cycle, and oxidative phosphorylation). By contrast, when glycolysis is blocked in glycolytic tumor cells, the tumor cells would die because of an inability to utilize the aforementioned pathways.

However, current glycolytic inhibition approaches for cancer treatment present various challenges. For instance, many such treatments are not specific for the hypoxic environment of tumor cells. More importantly, current treatments are not selective inhibitors of glycolysis. Rather, such treatments can also target other pathways that are essential for normal cell function, such as glycosylation, where monosachamides such as D-mannose are linked to proteins to form glycoproteins. Among other functions, glycoproteins are essential for maintaining the structural integrity of cell membrane.

Thus, interference with glycosylation can have clinical consequences. A need exists, therefore, for cancer treatments by the selective inhibition of glycolysis that do not substantially interfere with other metabolic pathways in the cell. Furthermore, there is currently an unmet need for the development of methods to treat cancer by molecules that demonstrate specificity for hypoxic cells. The present invention addresses these unmet needs.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, references to "glycolysis inhibitor," "glycolytic inhibitor" or "inhibitor(s) of glycolysis" are intended to refer to compounds or compositions that substantially inhibit or interfere with the activity of one or more enzymes involved in glycolysis.

As used herein, reference to "inhibition of glycolysis" is intended to refer to a decrease in glycolytic activity, a reduction in glycolytic activity, or the elimination of glycolytic activity.

As used herein, reference to "$IC_{50}$" is intended to refer to the concentration of a compound or composition that reduces the viability of cells to half the original level. In broader terms, $IC_{50}$ can refer to half the maximal inhibitory concentration of a substance for inhibiting various biological processes.

As used herein, reference to "therapeutically effective" is intended to qualify the amount of active ingredients that is used in the treatment of a disease or disorder described in the present disclosure. This amount will achieve the goal of reducing or eliminating the said disease or disorder.

As used herein, reference to "treatment" of a patient is intended to refer to procedures or applications of the methods of the present invention to a patient in order to temporarily or permanently cure, reduce, mitigate, or ameliorate a condition or disorder described in the present disclosure.

As used herein, reference to "patient" is intended to refer to all mammals including but not limited to humans, cows, dogs, cats, goats, sheep, pigs, and rabbits. Preferably, the patient is a human.

As used herein, reference to "inhibition of cell viability" is intended to refer to the reduction or elimination of cell division by various mechanisms, including but not limited to apoptosis, autophagy, and necrosis.

As used herein, reference to "hypoxic" is intended to refer to a condition characterized by low oxygen supply.

As used herein, reference to "normoxic" is intended to refer to a condition characterized by adequate oxygen supply.

As used herein, reference to "DFG" in intended to refer to 2-Deoxy-2,2-difluoro-D-arabino-hexopyranose, including any salt, ester or solvate thereof.

As used herein, reference to "2-DG" in intended to refer to 2-Deoxy-D-glucose.

All other terms as used herein are defined according to the ordinary meanings they have acquired in the art.

Therefore, provided herein are methods of treating gliomas by administering to a patient in need a therapeutically effective of amount of one or more of the compounds of Formulas I and II:

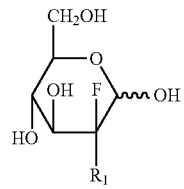

Formula I or a salt, or ester thereof, wherein:
R1 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;
R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and
R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

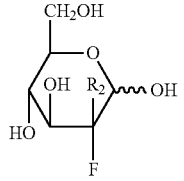

Formula II or a salt, or ester thereof, wherein:
R2 is selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_3R_4$, and $NHCOR_5$;

R3 and R4 are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and R5 is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH₂—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR₂ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH₃C(O) NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination; refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsinclude carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Current therapeutic options for treating glioma and other forms of highly glycolytic, hypoxic cancer cells, by inhibition of glycolysis, particularly those that do not induce toxicity, remain limited. For example, while studies indicate that 2-DG may be an inhibitor of glycolysis, the action of the molecule may also effect glycosylation pathways. For instance, certain studies indicate 2-DG interferes with N-linked glycosylation of viral coat glycoproteins, which interference can be reversed by the addition of mannose, a subtrate in many glycosylation pathways. In fact, some studies have even indicated that 2-DG elicits cell death by interfering with N-linked glycosylation, not glycolysis. *Molecular Cancer Therapeutics*. May 2007. 6(11):3049-058.

Therapeutic options for malignant gliomas also remain quite limited. This is due in part to the intrinsic resistance of the cells to many chemotherapy options that are available. It may also be due in part to the differential growth patterns which malignant gliomas exhibit. Namely, gliomas can grow in a predominately infiltrative fashion with little to no contrast enhancement seen on MRI scans versus more rapidly growing contrast enhancing mass lesions. Many studies have indicated that these different types of growth patterns also represent various degrees of hypoxic regions within individual tumors. Relative hypoxic areas can be seen both in the center of the rapidly growing tumor mass, which often has regions of necrosis associated with this, as well as some relatively hypoxic regions within the infiltrative component of the tumor as well. Accordingly, some of these relatively hypoxic regions may have cells, which are cycling at a slower rate and may therefore be more resistant to many chemotherapy agents.

Specifically, 2-Deoxy-2,2-difluoro-D-arabino-hexopyranose (DFG) is defined by structural formula below:

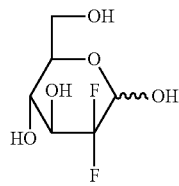

We have observed that 2-Deoxy-2,2-difluoro-D-arabino-hexopyranose (herein referred to as "DFG") inhibits the growth of glioma cells by inhibiting glycolysis in hypoxic cells without inhibiting glycoslyation (as in 2-DG). In inhibiting the glycolytic pathway with substantial selectivity, DFG treatment can substantially avoid clinical side-effects that are associated with disruptions in other metabolic pathways, such as glycosylation. Thus, DFG can inhibit glycolysis with less toxicity and be better tolerated.

Figure 6A:
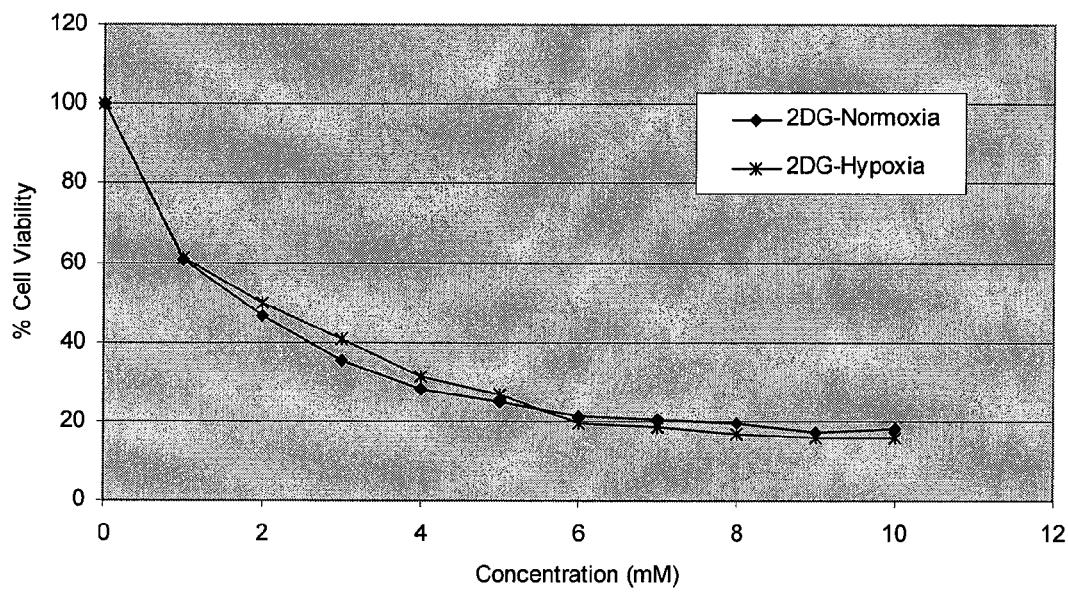
FIGS. 6a and 6b shows comparisons of 2-DG treatment in U87 GBM brain tumor cell line under normoxia and hypoxia performed in three independent experiments.
Figure 6B:
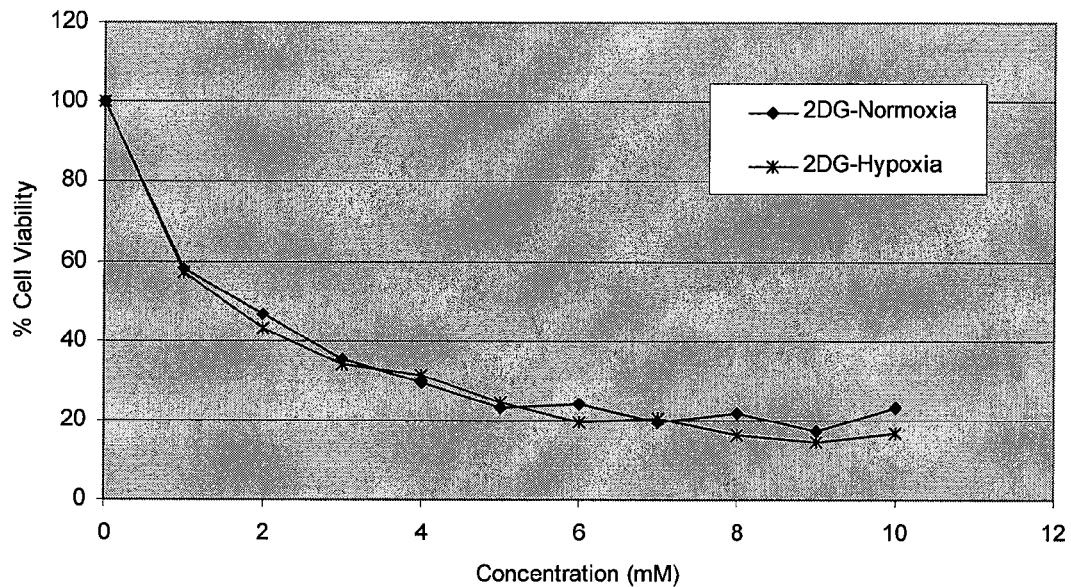

The unexpected therapeutic advantages of DFG in treating glioma and other forms of cancer are best illustrated by reference to various experiments, where we directly compared the effects of DFG with 2-DG on the viability of U87 glioblastoma tissue culture cells under various conditions. For instance, through viability assays shown in the graphs in FIG. 5, we observed that DFG decreased the viability of U87 glioblastoma cells in a dose-dependent manner. Furthermore, we unexpectedly observed that the effect of DFG was more potent under hypoxic conditions, as indicated by a lower $IC_{50}$ value. Conversely, as shown in FIG. 6, the effect of 2-DG on cell viability remained substantially the same under both hypoxic and normoxic conditions.

The table below summarizes and quantifies these results in terms of $IC_{50}$ values, which generally correspond to 2-DG or DFG concentrations that inhibited the viability of U87 glioblastoma cells to half their original level (i.e., 50%).

TABLE 1

Inhibition of U87 Cell Viability Under Hypoxia and Normoxia

| Treatment | Inhibition under Hypoxia | Inhibition under Normoxia |
|---|---|---|
| DFG | ++ | + |
| 2-DG | + | + |

++ $IC_{50}$ ~1.5-1.8 mM
+ $IC_{50}$ ≥1.8 mM

Figure 7A:
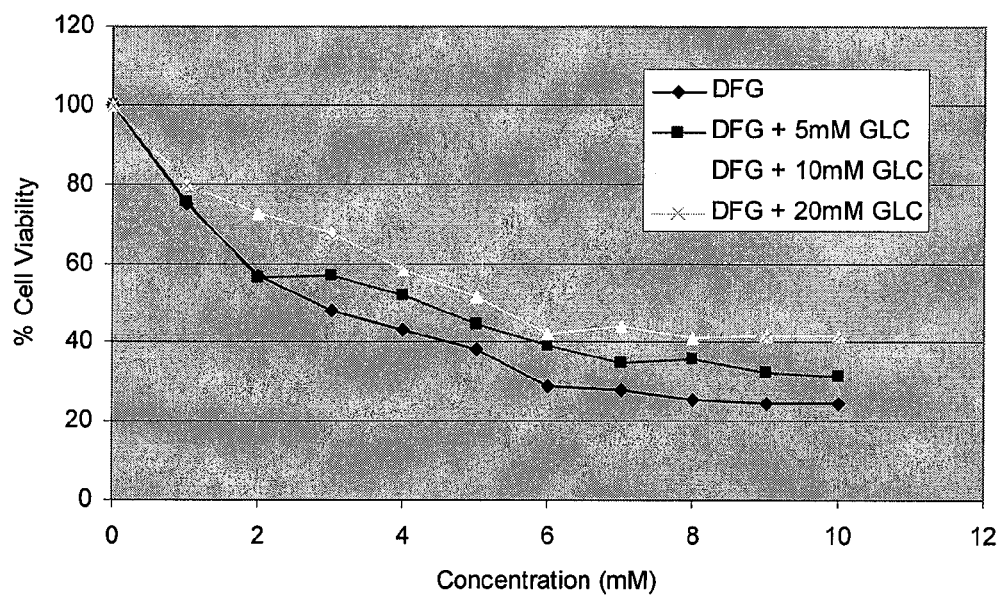
FIG. 7a shows U87 GBM brain tumor sensitivity to DFG alone and in the presence of increased concentration of D-glucose (GLC) under normoxia. D-Glucose protects moderately U87 glioblastoma from DFG-inhibited glycolysis in a dose dependent manner in normoxic conditions.
Figure 7B:
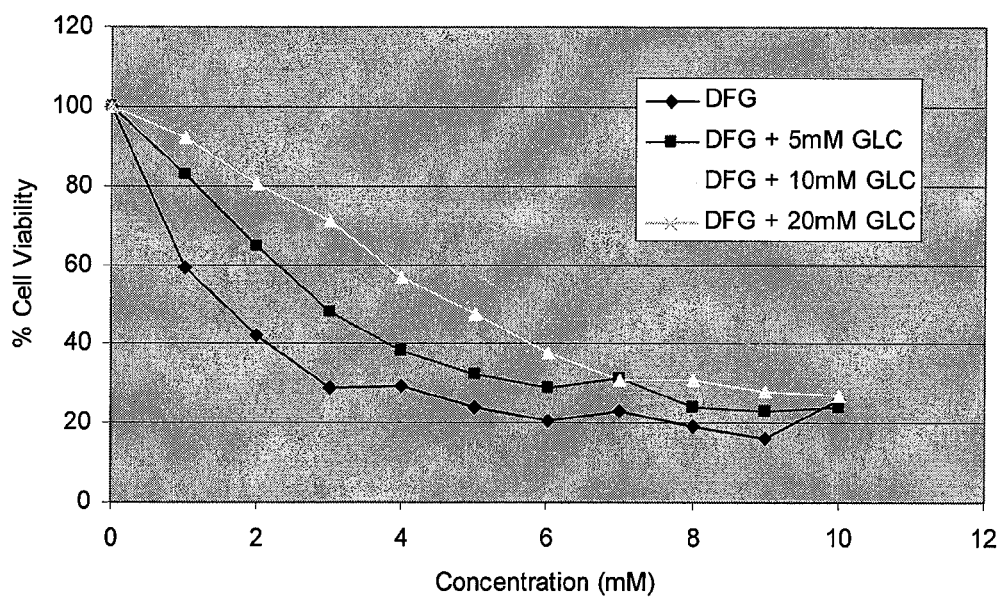
FIG. 7b shows U87 GBM brain tumor sensitivity in vitro to DFG alone and in the presence of increased concentrations of D-glucose (GLC) under hypoxia. D-Glucose protects U87 glioblastoma from DFG-inhibited glycolysis in a dose-dependent manner in hypoxic conditions to a greater extent than in normoxic conditions. Note the significant shift of $IC_{50}$ for DFG when D-Glucose is present.

In similar assays, DFG was shown to effect cell viability by inhibiting glycolysis. As shown in the graphs in FIG. 7, we observed that D-glucose protects the viability of U87 glioblastoma cells against DFG activity under both normoxic (FIG. 7a) and hypoxic (FIG. 7b) conditions in a dose-dependent manner, as indicated by significant shifts in $IC_{50}$ values after glucose co-treatment. Similar observations were made when glioblastoma cells were treated with 2-DG in the presence of glucose (FIG. 8). The table below summarizes and quantifies these results in terms of $IC_{50}$ values.

TABLE 2

Inhibition of U87 Cell Viability under Hypoxia and Normoxia in the Presence of Glucose

| Treatment | Viability Protection by D-Glucose Under Hypoxia | Viability Protection by D-Glucose Under Normoxia |
|---|---|---|
| DFG | ++ | + |
| 2-DG | +++ | + |

Figure 9A:
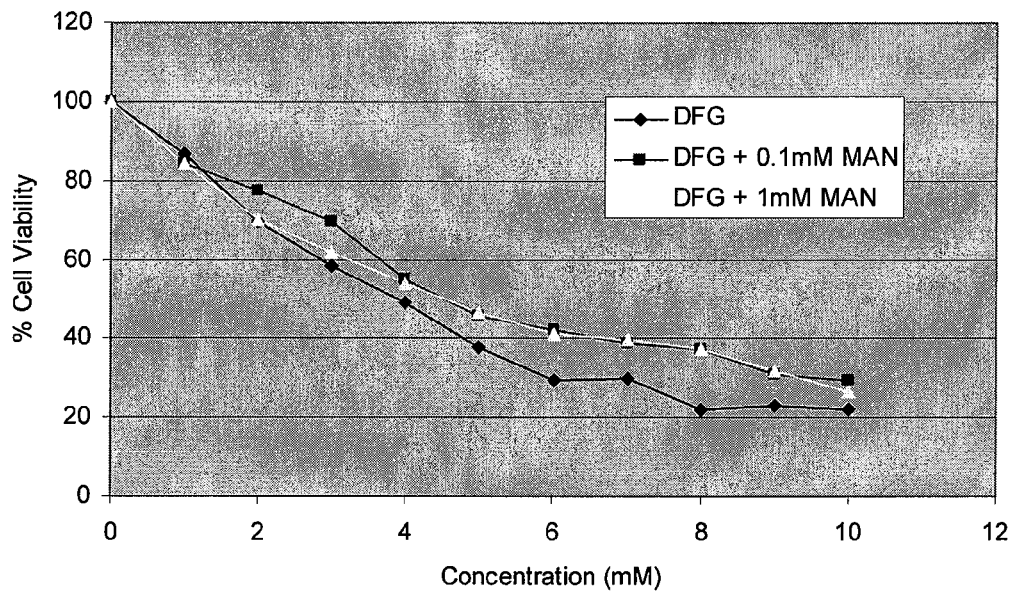
FIG. 9a shows U87 GBM brain tumor sensitivity in vitro to DFG alone and in the presence of increased concentration of D-mannose (MAN) under normoxia. D-Mannose has only a small effect on DFG inhibition of U87 cell line growth under normoxic conditions. Such an effect was noted at low level exposure (0.1 mM) but did not increase at a 10 fold greater concentration (1 mM).
Figure 9B:
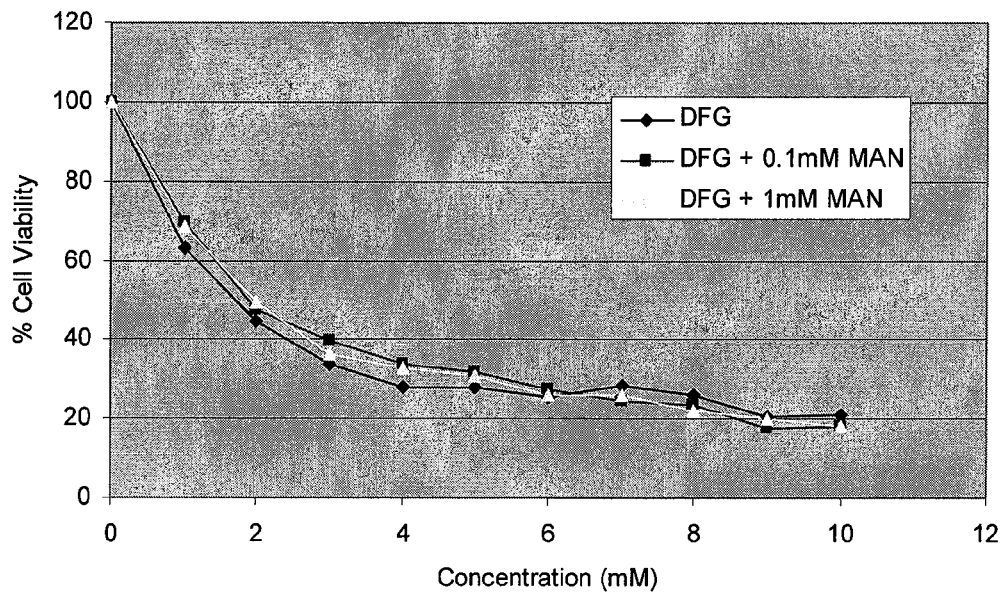
FIG. 9b shows U87 GBM brain tumor sensitivity in vitro to DFG alone and in the presence of increased concentration of D-mannose (MAN) under hypoxia. D-Mannose has no effect on DFG inhibition of U87 cell line growth under hypoxic conditions. Thus, under hypoxic conditions, DFG inhibits glycolysis selectively and therefore targets selectively highly glycolytic tumor cells.

+ ~1 mM $IC_{50}$ shift after co-treatment with 5 mM of D-glucose
++ ~1.5-2 mM $IC_{50}$ shift after co-treatment with 5 mM of D-glucose
+++ >5 mM $IC_{50}$ shift after co-treatment with 5 mM of D-glucose More importantly, in similar assays, increasing the concentrations of D-Mannose did not significantly affect the viability of glioblastoma cells against DFG activity under hypoxic or normoxic conditions, as demonstrated by an insignificant shift in $IC_{50}$ values after co-treatment with D-mannose. The graphs for such assays are shown in FIG. 9.

Figure 10A:
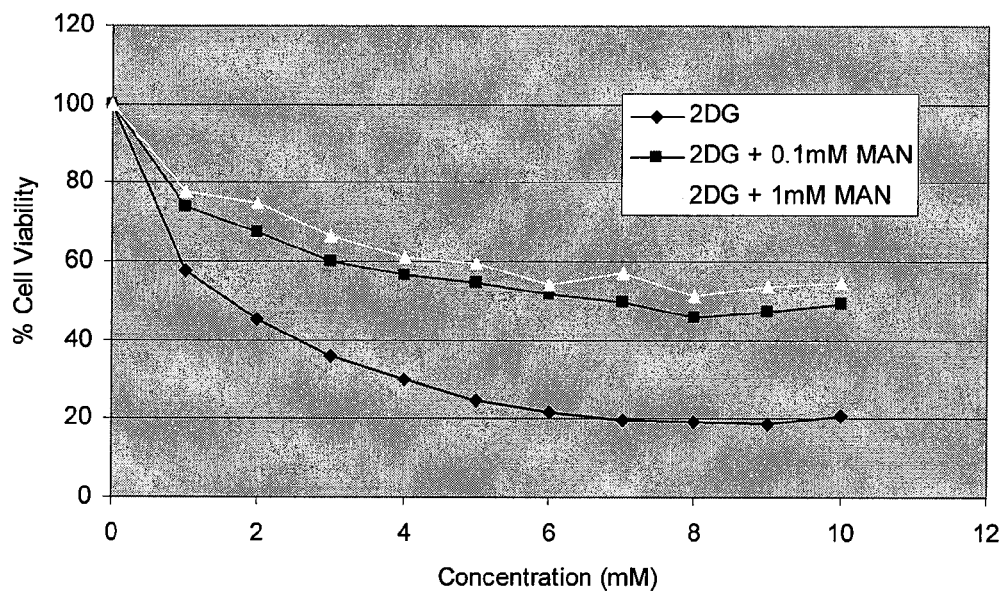
FIG. 10a shows U87 GBM brain tumor sensitivity in vitro to 2-DG alone and in the presence of increased concentration of D-mannose (MAN) under normoxia. D-Mannose offers significant protection to U87 glioblastoma from 2-DG-mediated growth inhibition in a non-dose dependent manner under normoxic conditions. In contrast to D-glucose protection, even low level D-Mannose exposure (0.1 mM) provides an equivalent degree of protection to 1 mM exposures. This is in contrast to DFG treatment where D-mannose effect was low.

However, as shown in FIG. 10, D-mannose showed significant protection to glioblastoma cells against 2-DG activity in a dose-independent manner under both normoxic and hypoxic conditions. The table below summarizes and quantifies these results in terms of $IC_{50}$ values.

TABLE 3

Inhibition of U87 Cell Viability Under Hypoxia and Normoxia in the Presence of D-Mannose

| Treatment | Viability Protection by D-Mannose Under Hypoxia | Viability Protection by D-Mannose Under Normoxia |
|---|---|---|
| DFG | − | + |
| 2-DG | ++ | +++ |

− 0-0.5 mM $IC_{50}$ shift after co-treatment with 0.1 mM of D-mannose
+ ~1 mM $IC_{50}$ shift after co-treatment with 0.1 mM of D-mannose
++ ~1.5-2 mM $IC_{50}$ shift after co-treatment with 0.1 mM of D-mannose
+++ >5 mM $IC_{50}$ shift after co-treatment with 0.1 mM of D-mannose Therefore, D-glucose offers protection to glioblastoma cells against 2-DG and DFG because both molecules compete with D-glucose as substrates for one or more enzymes in the glycolytic pathway, indicating that both molecules are inhibitors of glycolysis. However, the observation that D-mannose offers protection to glioblastoma cells against 2-DG activity indicates that 2-DG also competes with D-mannose as a substrate for one or more enzymes in glycosylation, further affirming that 2-DG is a non-selective inhibitor of glycolysis. Conversely, since D-mannose does not offer protection to glioblastoma cells against DFG activity, it is envisioned that DFG is not an inhibitor of glycosylation and a substantially selective inhibitor of the glycolytic pathway.

Figure 11A:
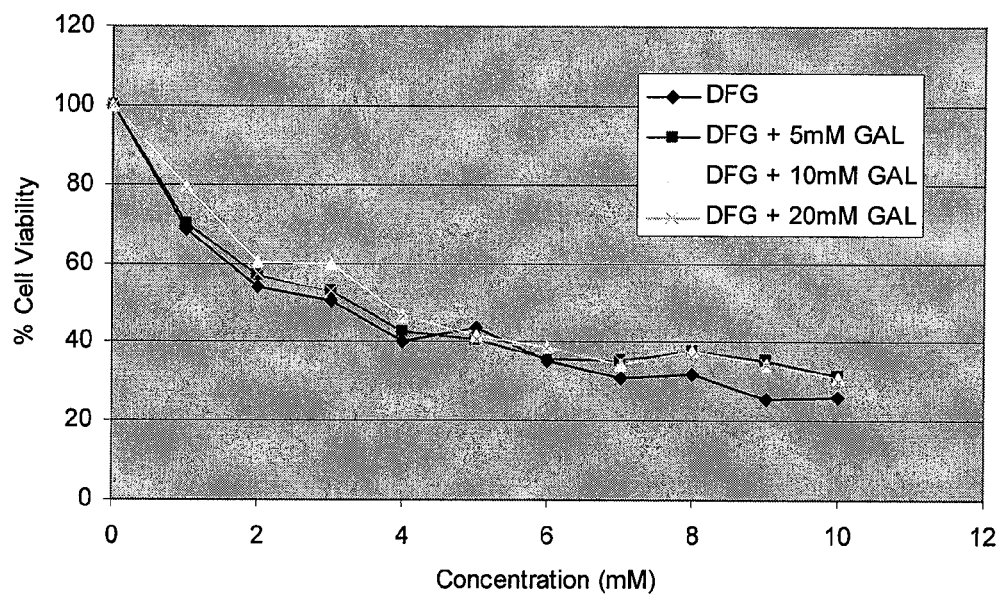
FIG. 11a shows U87 GBM brain tumor sensitivity in vitro to DFG alone and in the presence of increased concentration of D-galactose (GAL) under normoxia. D-Galactose supplementation has no impact on the survival of U87 glioblastoma cell from DFG-inhibited glycolysis, regardless of dose under normoxic conditions. Note that the $IC_{50}$ for DFG is unchanged and the curves are virtually super-imposable across the D-galactose concentration range.
Figure 11B:
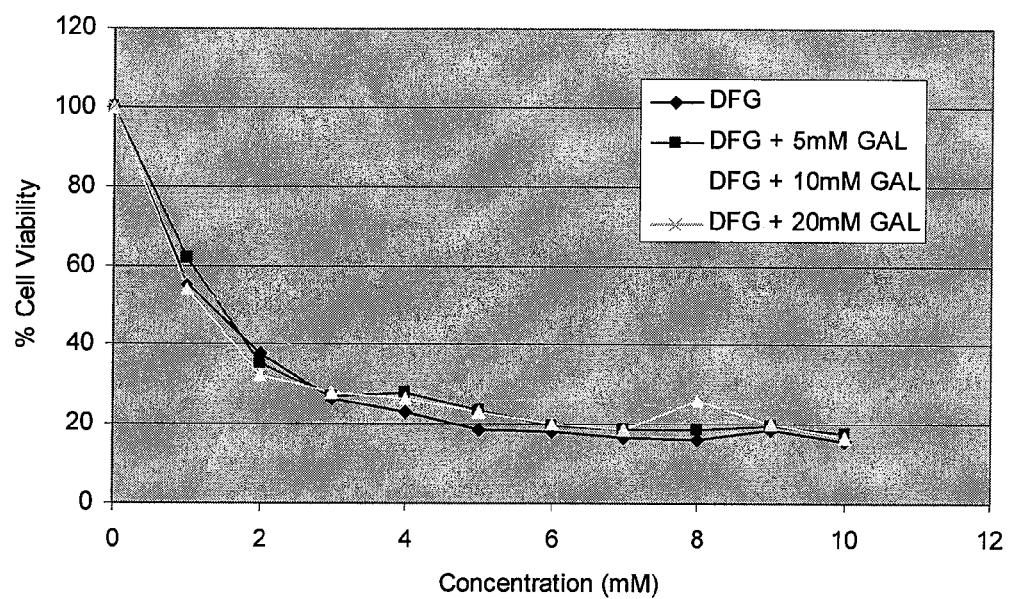
FIG. 11b shows U87 GBM brain tumor sensitivity in vitro to DFG alone and in the presence of increased concentration of D-galactose (GAL) under hypoxia. As with the hypoxic studies, D-galactose supplementation has no impact on the survival of U87 glioblastoma cell from DFG-inhibited glycolysis, regardless of dose. Note that the $IC_{50}$ for DFG is unchanged and the curves are virtually super-imposable across the D-galactose concentration rings.

The schematic diagram in FIG. 11 illustrates a model that provides a theoretical mechanism for the aforementioned DFG activity. As shown in the schematic, it can be envisioned that DFG only interferes with various glycolytic pathways, whereas 2-DG interferes with both glycolytic and glycosylation pathways.

Figure 12A:
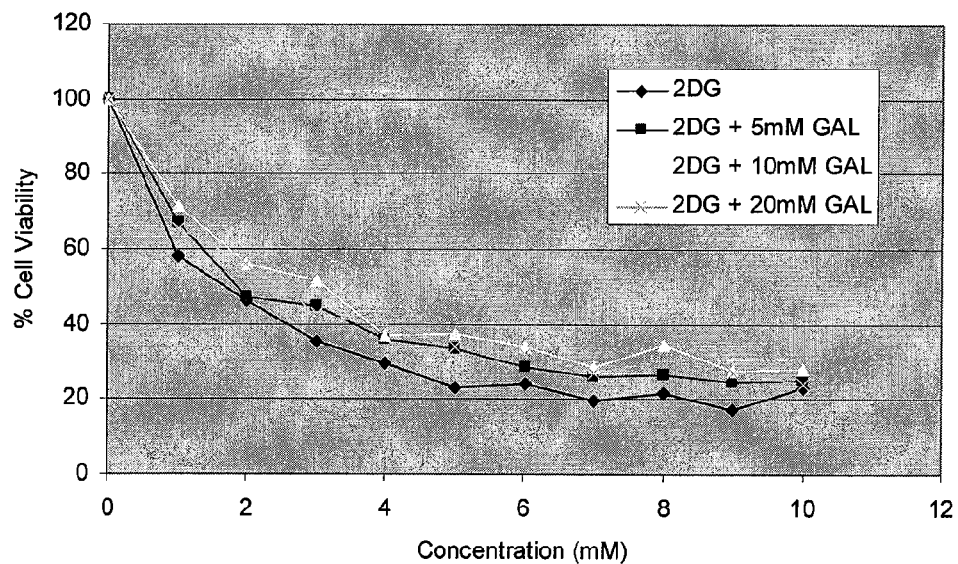
FIG. 12a shows U87 GBM brain tumor sensitivity in vitro to 2-DG alone and in the presence of increased concentration of D-galactose (GAL) under normoxia. D-Galactose supplementation has no impact on the survival of U87 glioblastoma cell from 2-DG-inhibited glycolysis, regardless of dose under normoxic conditions. Note that the $IC_{50}$ for DFG is unchanged and the curves are virtually super-imposable across the D-galactose concentration range.
Figure 12B:
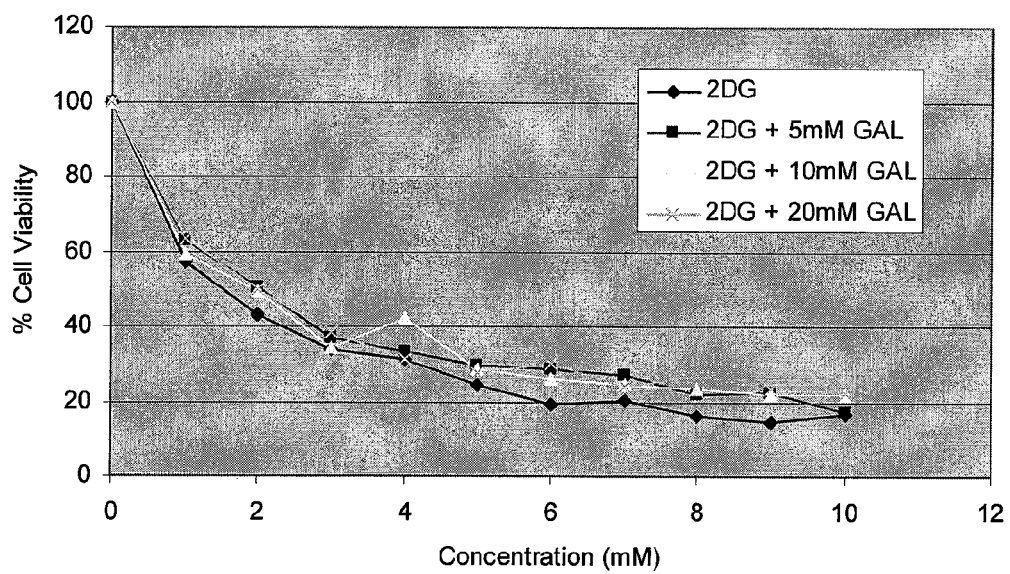
FIG. 12b shows U87 GBM brain tumor sensitivity in vitro to 2-DG alone and in the presence of increased concentration of D-galactose (GAL) under hypoxia. As with the normoxic studies, galactose supplementation has no impact on the survival of U87 glioblastoma cell from DFG-inhibited glycolysis, regardless of dose, under hypoxic conditions. Note that the $IC_{50}$ for DFG is unchanged and the curves are virtually super-imposable across the D-galactose concentration range.
Figure 13A:
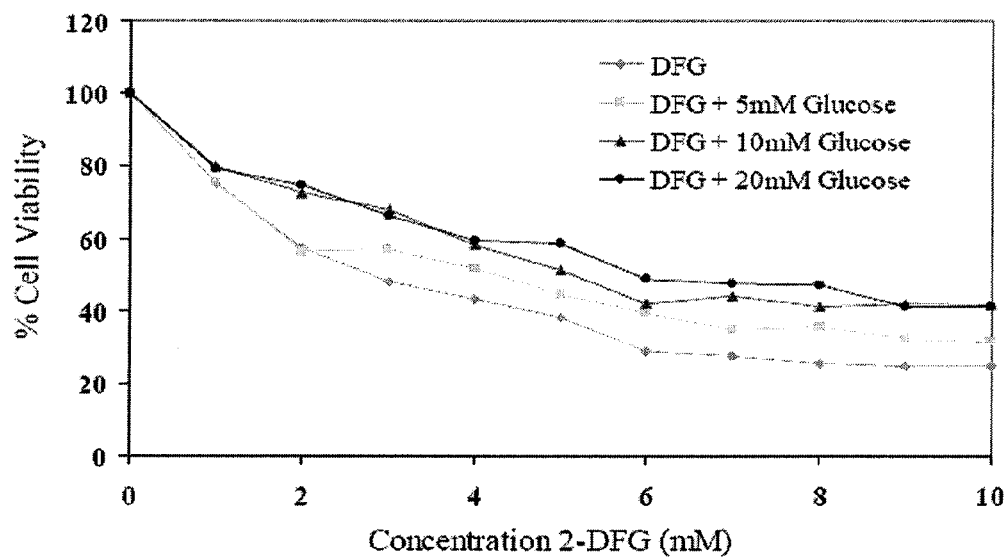
FIG. 13a shows the results of 2 DFG activity of 72 h normoxia treatment of U87 cells in vitro using MTT viability assay.
Figure 13B:
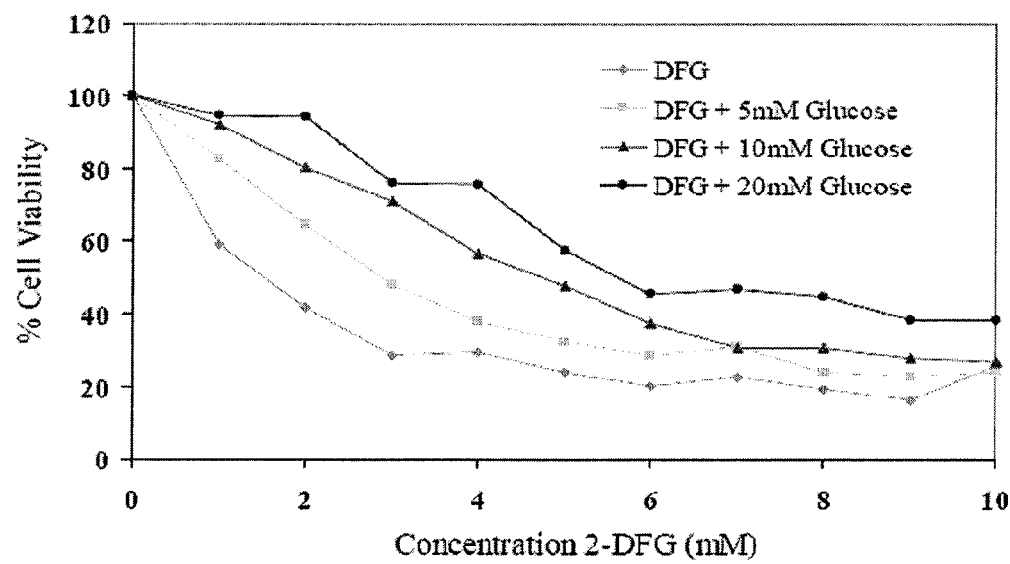
FIG. 13b shows the results of 2 DFG activity of 72 h hypoxia treatment of U87 cells in vitro using MTT viability assay.
Figure 14:
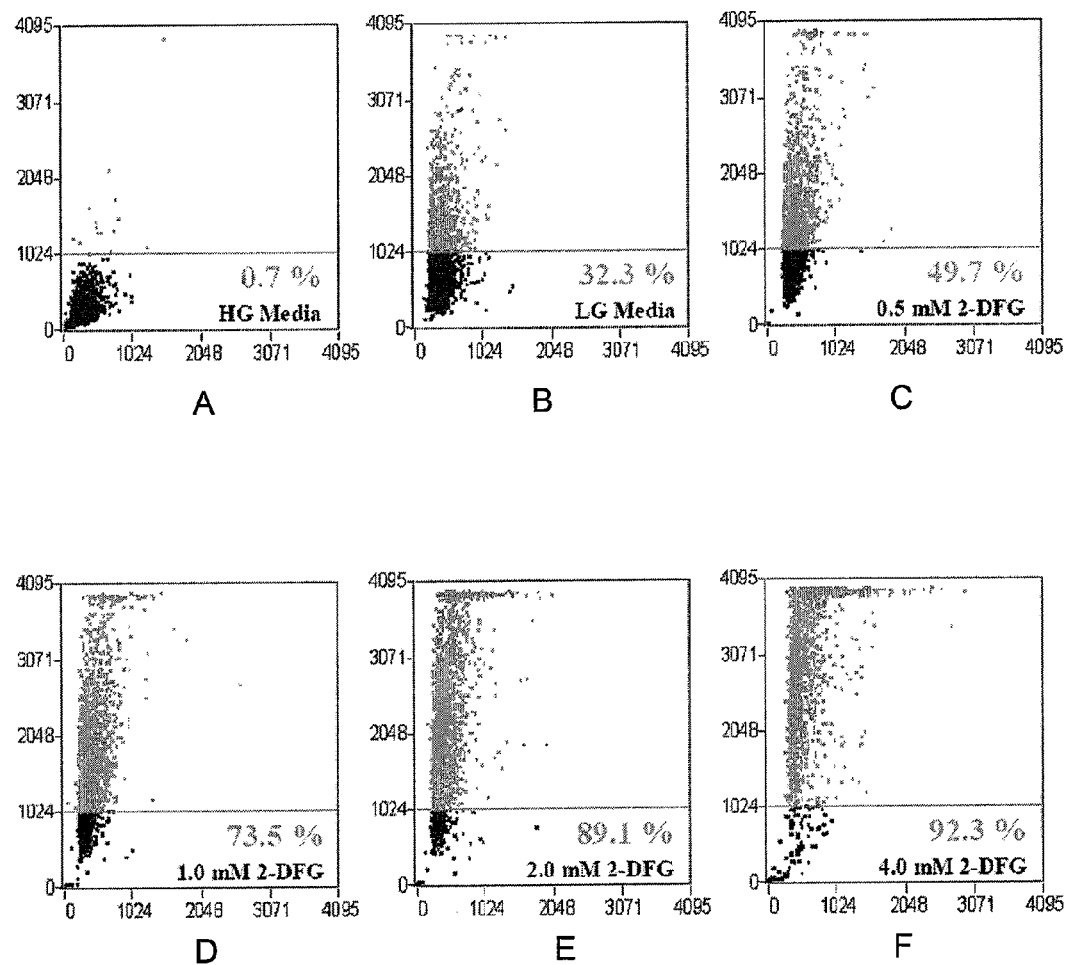
FIGS. 14a through 14f provide the quantification of 2-DFG induced autophagy in U87 glioma cells after 72 h of normoxia treatment in 5.6 mM low glucose media using acridine orange-acid vesicular organelles (AVO) straining assay.
Figure 15:
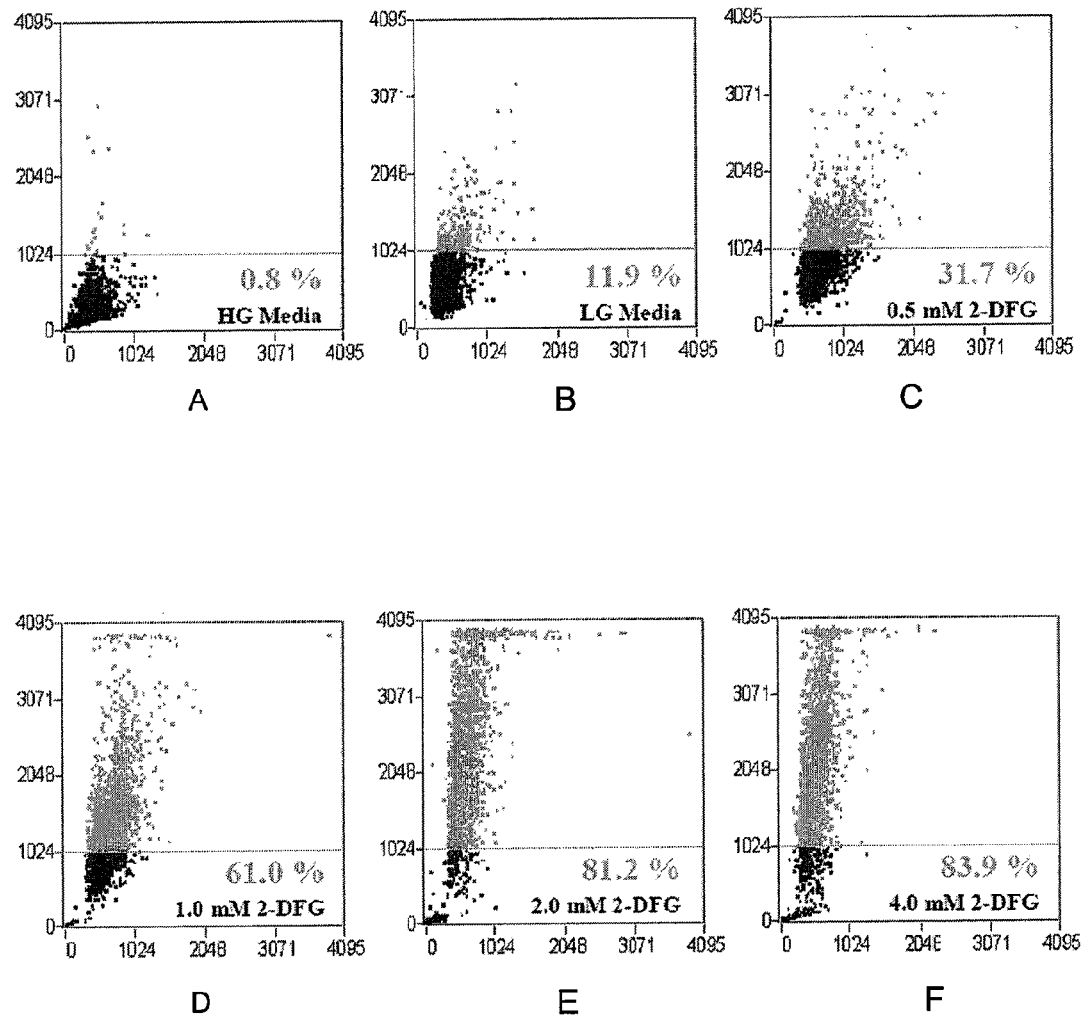
FIGS. 15a through 15f provide the quantification of 2-DFG induced autophagy in U87 glioma cells after 72 h of hypoxia treatment in 5.6 mM low glucose media using acridine orange-acid vesicular organelles (AVO) straining assay.
Figure 16:
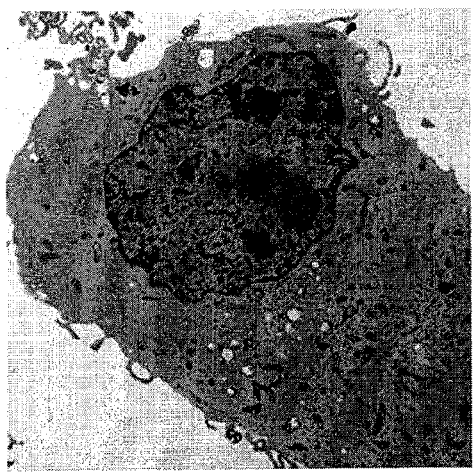
FIGS. 16a through 16d provides electron micrographs of 2-DFG induced autophagy in U87 cells (5 mM, 72 h treatment, 5.6 mM low glucose media).
Figure 16:
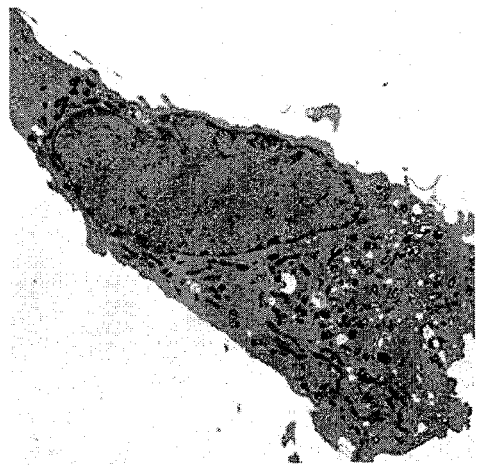
Figure 16:
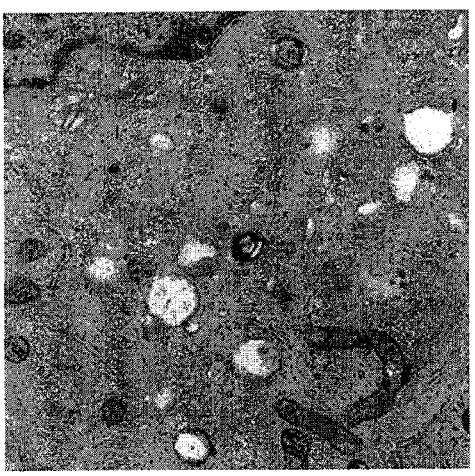
Figure 16:
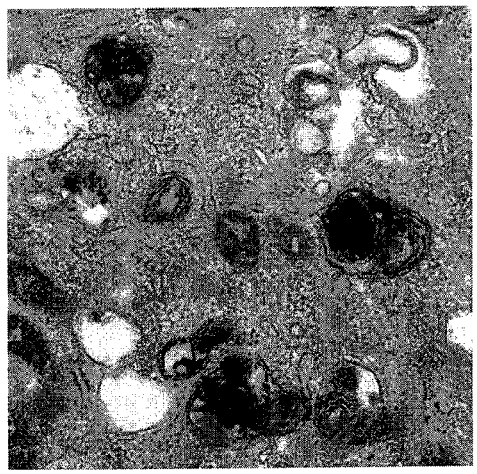
Figure 17:
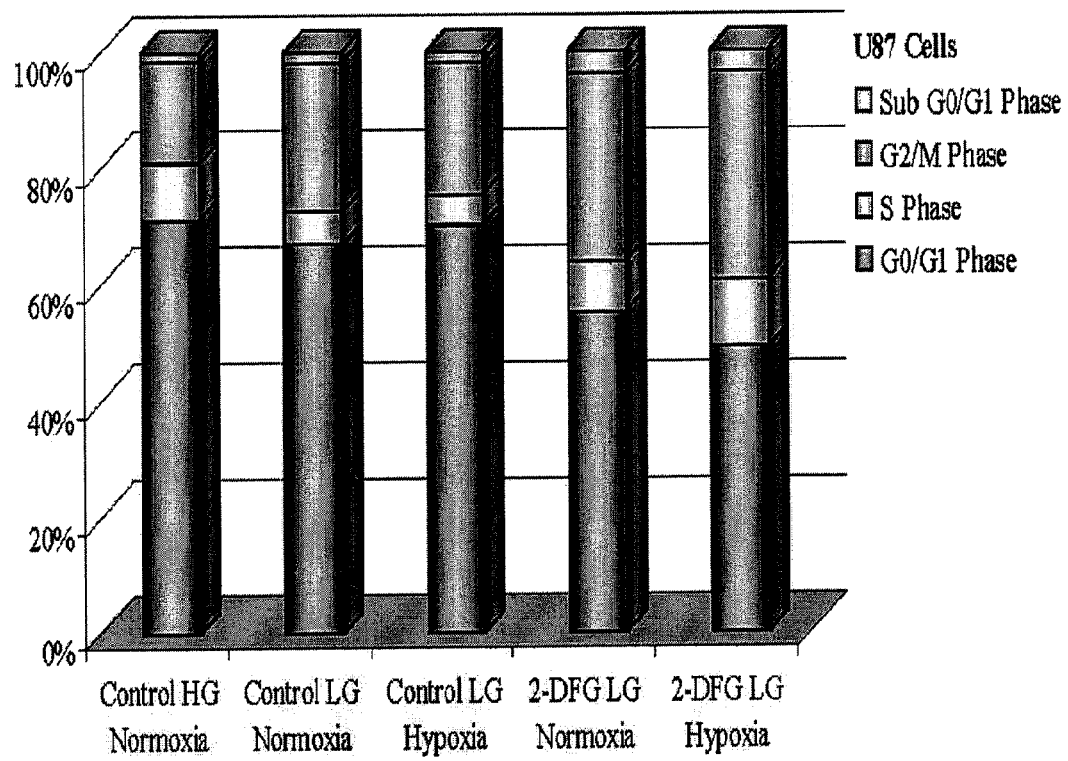
FIG. 17 shows the effect of 2-DFG (5 mM) on cell cycle distribution of U87 cells determined after 72 h treatment using cell cycle analysis.

Additional experiments confirmed that DFG is a substantially selective inhibitor of glycolysis. For instance, as shown in FIG. 11, the addition of various concentrations of D-galactose did not significantly affect the viability of glioblastoma cells against DFG activity under hypoxic and normoxic conditions. Similar results were obtained with 2-DG (FIG. 12). The table below summarizes these results.

TABLE 4

Inhibition of U87 Cell Viability Under Hypoxia and Normoxia in the Presence of D-Galactose

| Treatment | Viability Protection by D-Galactose Under Hypoxia | Viability Protection by D-Galactose Under Normoxia |
|---|---|---|
| DFG | − | − |
| 2-DG | − | − |

− 0-0.5 mM $IC_{50}$ shift after co-treatment with 5 mM of D-galactose.

It is noted that the aforementioned $IC_{50}$ values and ranges thereof are only estimates for the sole purpose of illustrating different activity levels under various conditions. Furthermore, the $IC_{50}$ values are not intended to confine the scope of the present invention in any way.

Without being bound by theory, it is envisioned that DFG exerts the aforementioned effects primarily by eliciting autophagy rather than apoptosis. Autophagy is a regulated process in which portions of the cytoplasm are first sequestered with double-membrane vesicles known as autophagosomes. Klionsky, D. J., et al., *Autophagy as a Regulated Pathway of Cellular Degradation*, Science, 2000, 290:1717-1721. These autophagosomes then fuse with lysosomes to become autolysosomes or degradative autophagic vacuoles, after which the sequestered contents are degraded by lysosomal hydrolases. Autophagy leads to the extensive degradation of organelles, including mitochondria, which precedes nuclear destruction.

Autophagy is induced in various cell conditions; for example, it is responsible for the degradation of normal proteins in response to nutrient deprivation, differentiation, aging, transformation, and cancer. Cuervo, A. M., *Autophagy: In Sickness and in Health*, Trends Cell Biol, 2004, 14: 70-77; Shintani, T., et al., *Autophagy in Health and Disease: A Double-Edged Sword*, Science, 2004, 306: 990-995. In cancer research, autophagy is a novel concept, and its role remains unclear. In general, cancer cells show less autophagic degradation than normal cells. Bursch, W., et al., *Programmed Cell Death (PCD). Apoptosis, Autophagic PCD, or Others?* Ann. N.Y. Acad. Sci., 2000, 926: 1-12; Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906. Indeed, Beclin1, a mammalian homologue of yeast autophagy-related gene Atg6, plays a role of a tumor suppressor. Liang, X. H., et al., *Induction of Autophagy and Inhibition of Tumorigenesis by Beclin* 1, Nature, 1999, 402: 672-676; Qu, X., et al., *Promotion of Tumorigenesis by Heterozygous Disruption of the Beclin* 1 Autophagy Gene, J Clin Invest, 2003, 112:1809-1820; Yue. Z., et al., *Beclin* 1, *an Autophagy Gene Essential For Early Embryonic Development, Is a Haploinsufficient Tumor Suppressor*, Proc Natl Acad Sci USA, 2003, 100: 15077-15082.

In contrast, numerous cancer treatments have been shown to induce autophagy in established cancer cell lines. Altan, N., et al., *Defective Acidification in Human Breast Tumor Cells and Implications for Chemotherapy*, J Exp Med, 1998, 187: 1583-1598; Paglin, S., et al., *A Novel Response of Cancer Cells to Radiation Involves Autophagy and Formation of Acidic Vesicles*, Cancer Res, 2001, 61: 439-444; Kanzawa, T., et al., *Induction of Autophagic Cell Death in Malignant Glioma Cells by Arsenic Trioxide*, Cancer Res, 2003, 63: 2103-2108; Daido, S., et al., *Inhibition of the DNA-Dependent Protein Kinase Catalytic Subunit Radiosensitizes Malignant Glioma Cells by Inducing Autophagy*, Cancer Res, 2005, 65:4368-4375; Takeuchi, H., et al., *Synergistic Augmentation of Rapamycin-Induced Autophagy in Malignant Glioma Cells by Phosphatidylinositol* 3-*Kinase/Protein Kinase B Inhibitors*, Cancer Res, 2005, 65:3336-3346. However, whether autophagy helps kill tumor cells or instead protects them from the treatments' cell-damaging effect is still debated. Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906; Edinger, A. L., et al. *Defective Autophagy Leads to Cancer*, Cancer Cell, 2003, 4:422-424; Kondo, Y., et al., *Role of Autophagy in Cancer Development and Response to Therapy*, Nat Rev Cancer, 2005, 5:726-734; Hait, W. N., et al., *A Matter of Life or Death (or Both): Understanding Autophagy in Cancer*, Clin Cancer Res., 2006 Apr. 1, 12(7 Pt 1):1961-5.

One of the main reasons why our understanding of autophagy's role in cancer is still fragmented is that methods to detect or quantify autophagy are limited. The gold standard is demonstration of autophagic vacuoles on electron microscopy; however, this analysis requires considerable skill and is neither easy nor quick. Other assays such as acridine orange or monodansyl cadaverine staining are not specific to autophagy. Paglin, S., et al., *A Novel Response of Cancer Cells to Radiation Involves Autophagy and Formation of Acidic Vesicles*, Cancer Res, 2001, 61: 439-444; Munafo, D. B., et al., *A Novel Assay to Study Autophagy: Regulation of Autophagosome Vacuole Size by Amino Acid Deprivation*, J Cell Sci, 2001, 114:3619-29. The use of the green-fluorescent protein (GFP)-tagged-rat microtubule-associated protein 1 light chain 3 (LC3) expression vector makes autophagy detection specific and easy, but this assay requires gene transfection and is not available for xenograft models or surgical specimens obtained from cancer patients. Kabeya, Y., et al., *LC3, a Mammalian Homologue of Yeast Apg8p, Is Localized in Autophagosome Membranes After Processing*, EMBO J, 2000, 19:5720-5728; Mizushima, N., et al., *Dissection of Autophagosome Formation Using Apg5-Deficient Mouse Embryonic Stem Cells*, J Cell Biol, 2001, 152:657-668.

Nonetheless, preliminary studies indicate that hexose compounds (such as 2-DG) are able to stimulate the process of autophagy in U87 Glioblastoma cells, as determined by the detection of autophagosomes in the cells after treatment. Thus, without again being bound by theory, it is envisioned that DFG also exerts its effects by autophagy.

The compounds presented herein can be used to treat glioma. These compounds can be used to treat other highly glycolytic forms of cancer, including but not limited to pancreatic cancer.

The methods provided herein can be used in various forms of treatment. For instance, while it may be possible for the compounds to be administered as a raw chemical, it is also possible to present it as a pharmaceutical formulation. Accordingly, the subject invention can include a pharmaceutical formulation comprising the compound or a pharmaceutically acceptable salt, ester, or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association the compound ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of DFGs to allow for the preparation of highly concentrated solutions.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds presented herein may be administered orally or via injection at a dose of from 0.1 to 4 g/kg per day. The dose range for adult humans is generally from 5 mg to 4 g/kg per day. Tablets or other forms of presentation provided in discrete units may conveniently contain an amount of compound of the invention which is effective at such dosage or as a multiple of the same, for instance, units containing 5 mg to 100 mg, usually around 10 mg to 10 g.

The amount of the compound that may be combined with the carrier materials to produce a single dosage form will vary depending upon the host treated and the particular mode of administration.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Besides being useful for human treatment, the compounds are also useful for veterinary treatment of companion animals, exotic animals and farm animals, including mammals, rodents, and the like. More preferred animals include horses, dogs, and cats.

In other embodiments, any one of the aforementioned modes of treatment can occur by providing clinicians with a kit that contains a therapeutically effective amount of compound in any of the aforementioned forms along with instructions on how to administer treatment to patients.

In certain instances, it may be also be appropriate to administer compound in combination with another therapeutic agent. By way of example only, if one of the side effects experienced by a patient upon receiving one of compound herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of compounds described herein with another therapeutic agent (which also includes a therapeutic regimen) that also has therapeutic benefit. By way of example only, in a treatment for diabetes involving administration of one of compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Reference will now be made to specific examples illustrating the methods above. It is to be understood that the examples are provided to illustrate preferred embodiments and that no limitation to the scope of the invention is intended thereby.

EXAMPLES

General Synthetic Methods for Preparing DFG

To test the effects of DFG on cancer cells, DFG was synthesized using the following general synthetic procedure set forth below.

Step 1: Synthesis of
1,2:5,6-di-O-isopropylidene-D-glucofuranose

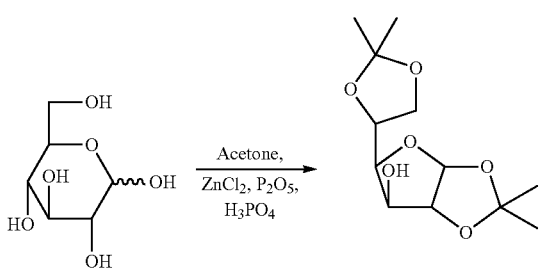

Zinc bromide (%) and $P_2O_5$ (20 g) were added to the previously prepared suspension of D-glucose (100 g) in acetone (2 L) and stirred overnight at room temperature. The pH of the reaction mixture was adjusted to 7 by addition of saturated water solution of sodium carbonate. Inorganic salts were filtered off and washed with acetone. Acetone solutions were combined and acetone was removed by evaporation. The resulting aqueous residue was extracted with ether (3×100 mL). Extracts were then pooled together and dried over $Na_2SO_4$. Drying agent and solvent were removed to give 85 g of 1,2:5,6-di-O-isopropylidene-D-glucofuranose. (Yield 60%). Additional information about this step appears in the *Journal of the American Chemical Society*, 1938, 60:1507. The entire article is incorporated herein by reference.

Step 2: Synthesis of 3-O-benzyl-1,2; 5,6-di-O-isopropylidene-D-glucofuranose

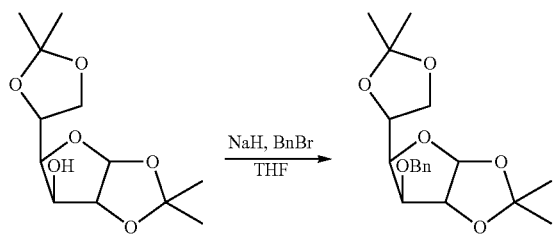

A suspension of sodium hydride (60% dispersion in oil) (8.5 g) and tetrabutylammonium iodide (0.5 g) in tetrahydrofuran (70 mL) was prepared and cooled down to 0° C. A solution of diacetone-D-glucose (50 g) in tetrahydrofuran (130 mL) was added dropwise and the mixture was stirred vigorously while it was allowed to rise up to ambient temperature. Benzyl bromide (25 mL) was added, and the reaction mixture was heated to 50° C. and stirred at that temperature for 2 hours. Methanol (50 ml) was added and the mixture was stirred for 2 hours, then it was cooled to room temperature, and filtered through Celite. Filtrate was evaporated to dryness. Resulting oil was dissolved in dichloromethane (150 mL), and obtained solution was washed with water (2×50 mL), then dried over $Na_2SO_4$. Drying agent was filtered off and solvent was evaporated to give 67 g of 3-O-benzyl-1,2; 5,6-di-O-isopropylidene-D-glucofuranose (Yield 100%). The product was not further purified. Additional information about this step appears in *Tetrahedron Asymmetry*, 1994, 5(3): 413-440. The entire article is incorporated herein by reference.

Step 3: Synthesis of 4-O-benzyl-D-glucopyranose

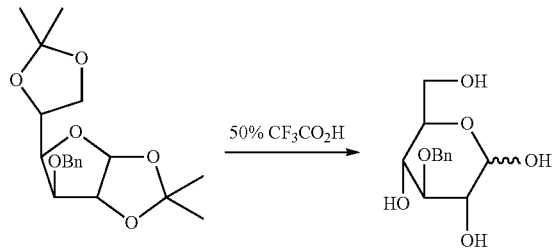 [SMILES: CC1(C)OCC(C2OC3OC(C)(C)OC3C2OCc2ccccc2)O1 ; OCC1OC(O)C(O)C(OCc2ccccc2)C1O]

The mixture of crude 3-O-benzyl-1,2; 5,6-di-O-isopropylidene-D-glucofuranose (67 g) in 50% aqueous trifluoroacetic acid (100 mL) was prepared and stirred at room temperature overnight. After the reaction was completed, the solvent was evaporated to dryness. The residue was then dissolved in water (100 mL) and the obtained solution was washed with a mixture of ethyl acetate and ether (5:1, v/v, 100 mL). Subsequently, the mixture was evaporated to dryness to give 42 g of 4-O-benzyl-D-glucopyranose (Yield 82%). The product was dried under reduced pressure and used in the next step without further purification. Additional information about this step appears in *Tetrahedron Asymmetry*, 1994, 5(3):413-440. The entire article is incorporated herein by reference.

Step 4: Synthesis of 1,2,4,6-tetra-O-acetyl-3-O-benzyl-α-D-glucopyranose

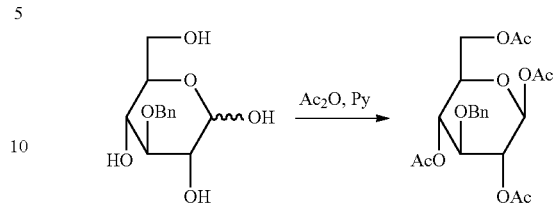

The 42 g of 4-O-benzyl-D-glucopyranose from Step 3 was dissolved in pyridine (200 mL). Acetic anhydride (75 mL) was then added, and the reaction mixture was stirred at room temperature overnight. Next, ethyl acetate (500 mL) was added. Subsequently, the mixture was first washed with a saturated water solution of sodium bicarbonate and then with water and brine. The washed solution was then dried over sodium sulfate. Inorganic salt was filtered off, and the solvent was evaporated to give 69 g of 1,2,4,6-tetra-O-acetyl-3-O-benzyl-α-D-glucopyranose. (Yield 100%). The crude product was used in the next step without further purification.

Step 5: Synthesis of 2,4,6-tri-O-acetyl-3-O-benzyl-α-D-glucosyl bromide

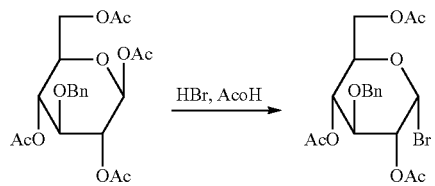

Hydrogen bromide (33% solution in acetic acid) (100 mL) was slowly added to the 69 g of 1,2,4,6-tetra-O-acetyl-3-O-benzyl-α-D-glucopyranose from Step 4 and cooled to 0° C. to produce a solution of 1,2,4,6-tetra-O-acetyl-3-O-benzyl-β-D-glucopyranose (70 g) in acetic acid (140 mL). The mixture was stirred at 0° C. for 1 hour and then diluted with chloroform (1 L). Next, the reaction mixture was washed with water and saturated sodium bicarbonate and then dried over sodium sulfate. The drying agent and solvent were removed to obtain crude 2,4,6-tri-O-acetyl-3-O-benzyl-α-D-glucosyl bromide. The product was used in the next step without further purification. Additional information about this step appears in *Journal of Organic Chemistry*, 1962, 3089-3092. The entire article is incorporated herein by reference.

Step 6: Synthesis of benzyl 2,4,6-tri-O-acetyl-4-O-benzyl-β-D-glucopyranoside

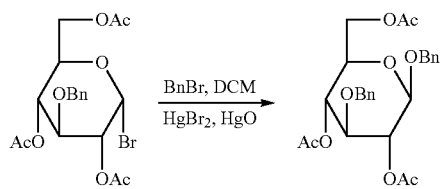 [SMILES: CC(=O)OCC1OC(Br)C(OC(C)=O)C(OCc2ccccc2)C1OC(C)=O ; CC(=O)OCC1OC(OCc2ccccc2)C(OC(C)=O)C(OCc2ccccc2)C1OC(C)=O]

The mixture of benzyl alcohol (35 g), HgBr$_2$ (17 g), HgO (70 g), and molecular sieves 4A in dichloromethane (300 mL) was prepared and stirred at room temperature for 2 hours. The solution of crude 2,4,6-tri-O-acetyl-3-O-benzyl-β-D-glucopyranosyl bromide in dichloromethane from Step 5 was then added to the mixture, and the reaction was stirred at room temperature for 30 min. After the reaction was completed, the mixture was filtered through Celite. Next, the Filtrate was evaporated to dryness and the crude product was used in the next step without further purification.

Step 7: Synthesis of benzyl 2-O-acetyl-3-O-benzyl-D-glucopyranoside

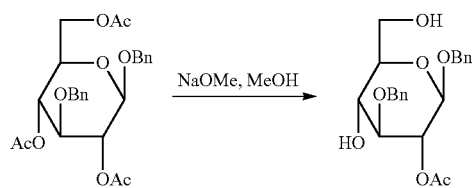 [SMILES: CC(=O)OCC1OC(OCc2ccccc2)C(OC(C)=O)C(OCc2ccccc2)C1OC(C)=O ; CC(=O)OC1C(OCc2ccccc2)OC(CO)C(O)C1OCc1ccccc1]

Crude benzyl 2,4,6-tri-O-acetyl-4-O-benzyl-D-glucopyranoside from Step 6 was dissolved in methanol (500 mL). Sodium methoxide (25% 2 mL) was then added to the obtained solution. Next, the reaction mixture was stirred at room temperature overnight. The pH of the reaction mixture was adjusted to 7 by addition of 1N HCl water solution. Subsequently, the solvent was evaporated to dryness, and crude benzyl 2-O-acetyl-3-O-benzyl-D-glucopyranoside was purified by column chromatography (SilicaGel 60) using chloroform—methanol 0-30% as eluents. 24 g of pure product was obtained. Additional information about this step appears in *Carbohydrate Research*, 1977, 59:268-273. The entire article is incorporated herein by reference.

Step 8: Synthesis of benzyl 3-O-benzyl-4,6-O-benzylidene-β-D-glucopyranoside

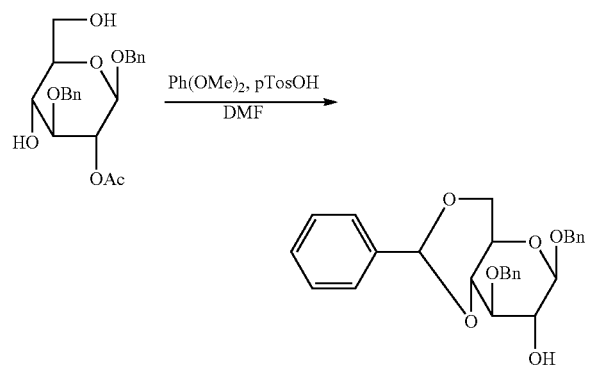

p-Toluenesulfonic acid monohydrate (150 mg) followed by dimethoxytoluene (20 mL) were added to a solution of 2-O-acetyl-3-O-benzyl-D-glucopyranoside (24 g) from Step 7 in DMF (200 mL). The obtained solution was heated to 50° C. for 3 hours while it was stirred under slightly reduced pressure. The reaction mixture was then cooled down and diluted with dichloromethane (1 L). Next, sodium bicarbonate was added, and the formed layers were separated. The organic layer was then washed with water and brine and dried over sodium sulfate. Finally, inorganic salts and solvents were removed, and the product was purified by crystallization from methanol. 22 g of benzyl 3-O-benzyl-4,6-O-benzylidene-β-D-glucopyranoside was obtained. (Yield 80%). Additional information about this step appears in *Carbohydrate Research*, 1083, 116:217-225. The entire article is incorporated herein by reference.

Step 9: Synthesis of benzyl 4,6-O-benzylidene-3-O-benzyl-β-D-arabino-hexapyranosis-2-ulose

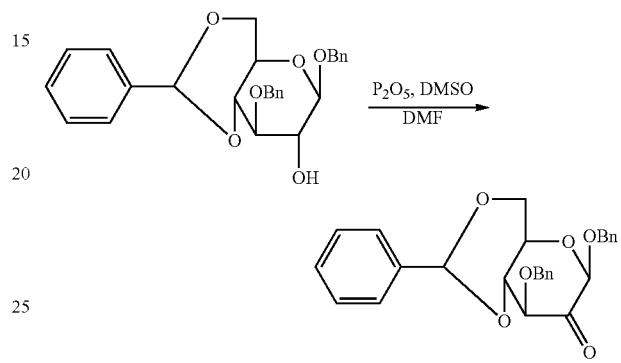

A mixture of benzyl 3-O-benzyl-4,6-benzylidene-D-glucopyranoside from Step 9 (6 g), DMF (120 mL), DMSO (60 mL), and phosphorus pentoxide (6 g) was prepared and stirred at 40° C. for 24 hours. The reaction mixture was then cooled down. Next, dichloromethane (200 mL) was added. The obtained solution was washed with saturated sodium bicarbonate and then with water until it was neutral. The solution was subsequently dried over sodium sulfate. The drying agent was then filtered off, and the solvent was evaporated. Finally, the product was purified by crystallization from ethanol. (Yield 3.8 g). Additional information about this step appears in *Carbohydrate Research*, 1977, 59:268-273. The entire article is incorporated herein by reference.

Step 10: Synthesis of benzyl-3-O-benzyl-4,6-O-benzylidene-2-deoxy-2,2-difluoro-D-arabino hexopyranoside

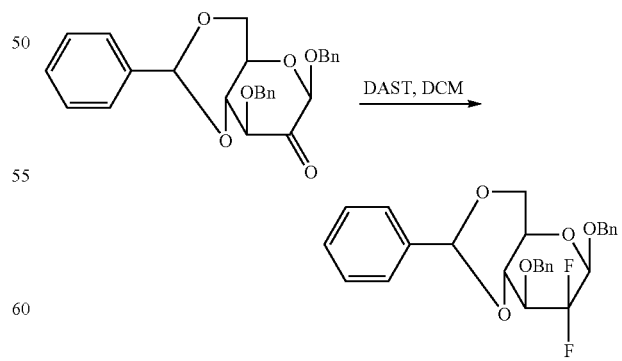

The ulose obtained from Step 9 (3.4 g) was dissolved in dichloromethane (20 mL). The solution was then flushed with nitrogen and cooled down to −40° C. Next, DAST (3 mL) was added dropwise, and the reaction mixture was slowly warmed up to room temperature. The solution was then stirred at room temperature for 2 hours. Subsequently, the reaction mixture was cooled down to 0° C. and poured into a mixture of sodium bicarbonate and dichloromethane that was previously cooled to 0° C. The mixture was then stirred for 2 hours while it warmed up to ambient temp. The formed layers were separated, and the water layer was extracted with dichloromethane. In addition, the combined organic solutions were dried over sodium sulfate. After the drying agent and solvent were removed, the crude product was purified by column chromatography (SilicaGel 60) using hexanes-ethyl acetate (0-40%) as eluents. 3 g of benzyl 3-O-benzyl-4,6-benzylidene-2,2-difluoro-2-deoxy-D-glucopyranoside was obtained. (Yield 80%). Additional information about this step appears in *Carbohydrate Research*, 1992, 233:$C_1$-$C_3$. The entire article is incorporated herein by reference.

Step 11: Synthesis of 2-deoxy-2,2-difluoro-D-arabino-hexopyranose

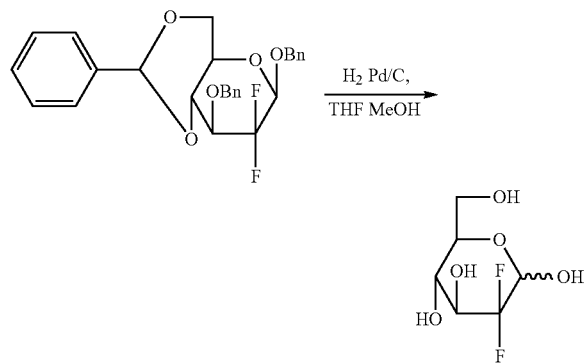

A solution of benzyl 3-O-benzyl-4,6-benzylidene-2,2-difluoro-2-deoxy-D-glucopyranoside (3 g) from Step 11 in the mixture of THF (10 mL) and methanol (20 mL) was prepared. Next, Pd/C 20% Degussa type (0.6 g) was added, and the substrate was hydrogenated using Paar apparatus under $H_2$ pressure (40 psi) for 24 hours. The reaction mixture was then filtered through Celite, and the filtrate was evaporated to dryness. The obtained product, 2,2-difluoro-2-deoxy-D-glucose, was purified by column chromatography (SilicaGel 60) using chloroform-methanol (0-30%) as eluents. About 1.2 g of pure product was obtained. Additional information about this step appears in *Carbohydrate Research*, 1971, 18:345-347. The entire article is incorporated herein by reference.

Mass spectral studies, incorporating separation of the DFG from putative impurities by liquid chromatography, demonstrated the purity of DFG produced by this synthesis was in excess of 95% and mass analysis confirmed by mass weight of the synthesized product to be 200.14 amu.

Biological Activity Assays

Cell viability experiments were carried out in U87 glioblastoma cells with 8000 cells/well in flat bottom 96 well plates. The cells were grown in low glucose (5.4 mM) DMEM/F12 media with 10% FBS and antibiotics. 24 hours after plating, cells were treated with increasing concentration of 2-deoxy-2,2-difluoro-D-arabino-hexopyranose (DFG) for 72 hours in normoxic (21% $O_2$) or hypoxic (0.1% $O_2$) conditions. In addition, to test the ability of monosachamides to compete with DFG in inhibiting glycolysis and glycosylation, cells were treated with increasing concentrations of glucose, mannose or galactose. The experiments were carried out in duplicate (n=2).

The effects of DFG on U87 glioblastoma cell lines challenged with D-glucose (FIG. 7) and with D-mannose (FIG. 9) demonstrated that the effects of D-glucose were significantly greater than that of D-mannose. Overall, the effects of D-mannose were negligible, while D-glucose significantly blocked the effects of DFG. These data clearly demonstrated that DFG acts as through the inhibition of glycolysis rather than by interfering with the biological processing of D-mannose during glycosylation.

Comparison of the effects of DFG under both normoxia and hypoxia (FIG. 5a-5c) indicate that U87 cells were significantly more sensitive to DFG under hypoxic conditions. Substantial inhibition of cellular growth was observed at DFG concentrations lower than 4 mM whereas under normoxic conditions concentrations above 6 mM were required for the same effect. Further, it should be noted that D-galactose, which does not affect the glycolysis process or mannose glycosylation under both hypoxia (FIG. 11b) or normoxia (FIG. 11a) had no effect on the ability of DFG to inhibit U87 GBM cell growth.

Figure 8A:
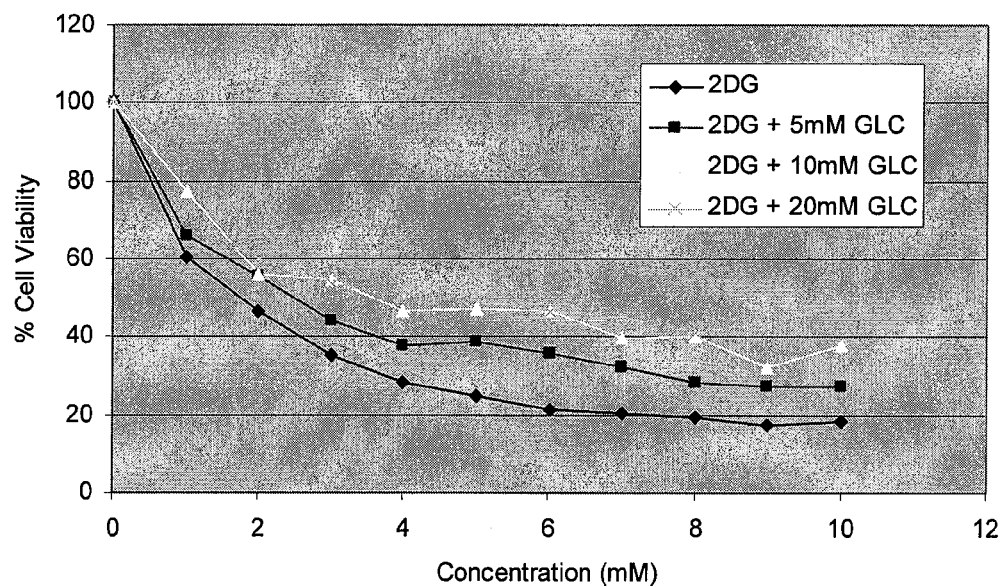
FIG. 8a shows U87 GBM brain tumor sensitivity in vitro to 2-DG alone and in the presence of increased concentration of D-glucose (GLC) under normoxia. D-Glucose protects U87 glioblastoma from 2-DG-inhibited glycolysis in a dose-dependent manner in normoxic conditions. Note the significant increase of $IC_{50}$ for 2-DG when D-glucose is present.
Figure 8B:
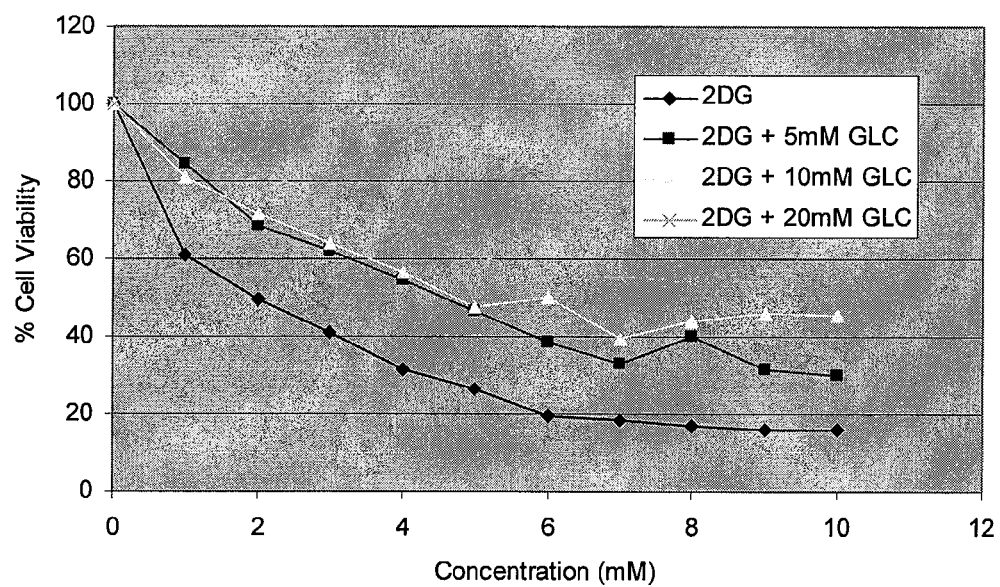
FIG. 8b shows U87 GBM brain tumor sensitivity in vitro to 2-DG alone and in the presence of increased concentration of D-glucose (GLC) under hypoxia. D-Glucose protects U87 glioblastoma from 2-DG-inhibited glycolysis in a dose-dependent manner in hypoxic conditions to a greater extent than in normoxic conditions. Note the significant increase of $IC_{50}$ for 2-DG when D-glucose is present.
Figure 10B:
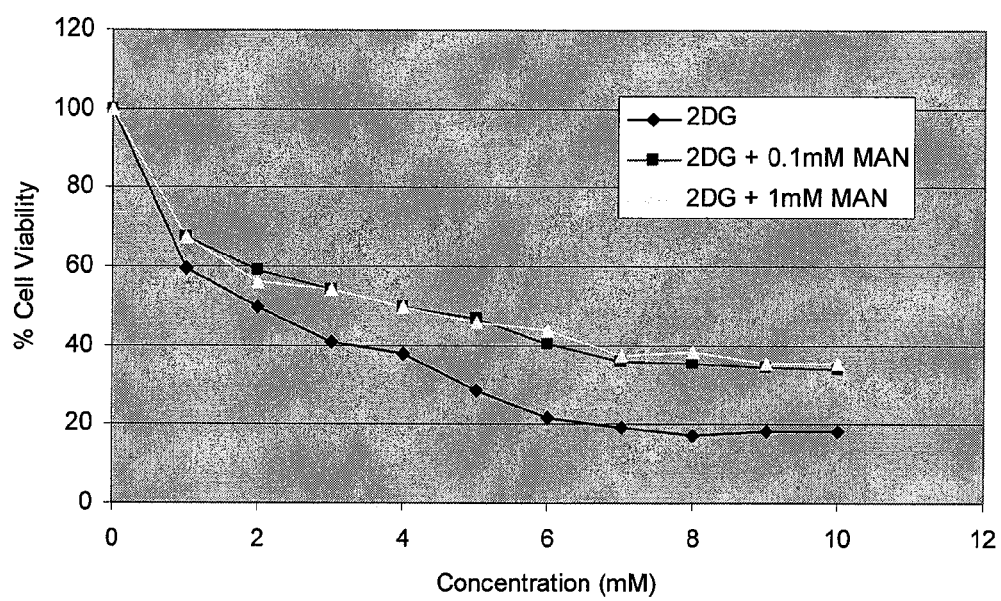

Furthermore, in similar experiments conducted for 2-DG, we clearly demonstrated that D-mannose effects the ability of 2-DG to inhibit cell growth under normoxia (FIG. 10a) and the effect was more pronounced than that of D-glucose itself under normoxia (FIG. 8a). To the contrary, under hypoxia, the effect of challenging 2-DG with D-glucose (FIG. 8b) were more pronounced than that of D-mannose itself (FIG. 10b). Thus 2-DG acts also through mechanisms other than glycolysis and such mechanisms are more pronounced in normoxia and might be harmful to normal cells.

The sum of these results indicate DFG acts primarily through the inhibition of glycolysis, in contrast to 2-DG, which exerts its action by targeting biological effects of D-glucose and D-mannose. These results demonstrate that DFG is a mechanistically pure compound (compared to 2-DG) that selectively targets glycolysis and as such should be a preferred agent to treat tumor cells that are metabolically altered to utilize glycolysis.

U87 human glioma cancer cells were obtained from the American Type Culture Collection (Manassas, Va.) and maintained in a humidified atmosphere containing 5% $CO_2$ at 37° C. Cells were routinely cultured in DMEM/F12 medium (Invitrogen Corp., Grand Island, N.Y.) supplemented with 10% heat inactivated fetal bovine serum (Hyclone Laboratories Inc., Logan, Utah), 50 IU/ml penicillin and 50 mg/ml streptomycin from GIBCO (Invitrogen). Cell viability experiments were carried out in U87 cells with 8000 cells/well in flat bottom 96 well plates. The cells were grown in low glucose (5.4 mM) DMEM/F12 media supplied with 10% FBS and antibiotics. 24 hours after plating, cells were treated with increasing concentration (1 to 10 mM) of 2-difluoro-D-glucose (DFG) for 72 hours in normoxic (21% $O_2$) or hypoxic (approximately 0.1% $O_2$) conditions. To test the competing ability of glucose, galactose and mannose with DFG, the cells were also treated with increasing concentration of the glucose (5, 10, and 20 mM), galactose (5, 10, and 20 mM) or mannose (0.1, 1, and 5 mM). The experiments were carried out in duplicate (n=2). After 72 hours of treatment, inhibition of cellular proliferation was assessed by the MTT assay. Absorbance was read at a wavelength of 570 nm using a V Max Micro plate reader by Molecular Devices, Inc. (Sunnyvale, Calif.). The cytoctoxicity of 2-DFG was calculated by normalization to the 100% viability of the control (untreated cells) and presented as percent control.

Glycolysis is the major energy producing pathway for fast growing, glycolytically depended tumors, such as gliomas. Blocking glycolysis is therefore an important therapeutic strategy when used alone or in combination therapy to enhance the effects of chemotherapy in energy starved tumors. We have examined D-glucose antimetabolites 2-deoxy-D-glucose (2-DG), 2-fluoro-2-deoxy-D-glucose (2-FG) and 2-fluoro-2-deoxy-D-mannose (2-FM) and confirmed their ability to block glycolysis and discovered their ability to induce autophagic cell death in vitro and established that their antitumor activity in vivo in orthotopic glioma model was comparable to that of temozolomide, the standard of care therapy. In order to determine a more selective inhibitor of glycolysis, we have synthesized 2-deoxy-2,2-difluoro-D-glucose (2-DFG) and initially assessed its ability to block glycolysis and induce autophagic cell death in comparison with our previously tested analogs. Cell viability assays were carried in U87 cells treated for 72 h with increasing concentrations of the 2-DFG under hypoxic and normoxic conditions. The results showed 2-DFG to have comparable cytotoxicity as that demonstrated by 2-DG, 2-FG and 2-FM in U87 cells treated for 72 h with $IC_{50}$ values of 2.9 mM in cells treated under normoxic conditions (21% $O_2$) and 1.2 mM, when cells were under hypoxic conditions (0.1% $O_2$).

To test the ability of the 2-DFG to induce autophagic cell death, we monitored the increase in acidic vesicular organelles (AVO) using acridine orange staining in U87 cells treated with increasing concentrations of 2-DFG for 72 hours under hypoxia and normoxia. The results showed concentration dependent increase in acridine orange staining indicating the increase in autophagic cell death. The confirmation of autophagy (Type II programmed cell death) in U87 cells following 5 mM 2-DFG treatment was demonstrated using transmission electron microscopy (TEM) showing the presence of multilamellar structures, otherwise called autophagosomes. Our studies show that 2-DFG is an equally potent inhibitor of cell proliferation and a potent inducer of autophagic cell death in gliomas as are 2-DG, 2-FG, and 2-FM. Therefore, targeting the energetic metabolism of cancer cells and the autophagic survival response using inhibitors of glycolysis is a promising therapeutic approach for the treatment of cancers that are dependent on glycolysis for survival.

The major energy producing mechanism for rapid growth of tumor cells in highly glycolytic cancers is glycolysis. In this study we investigated the ability of the glucose analog 2,2-difluoro-D-glucose (2-DFG) to inhibit glycolysis in U87 glioma cells causing energy deprivation and ultimately leading to autophagic cell death.

Our results show that 2-DFG activity in U87 gliomas is similar to that which we have previously reported for 2-deoxy-D-glucose (2-DG), 2-deoxy-2-fluoro-D-glucose (2-FG) and 2-fluoro-D-mannose (2-FM). The data show that 2-DFG inhibits glioblastoma cell growth under normoxic and hypoxic conditions in a dose dependent manner, and its cytotoxic effects are dependent on the glucose concentration in the media.

Acridine orange staining confirmed the marked increase in Acidic Vesicular Organelles (AVO) formation when cells were treated for 72 h with increasing concentrations of 2-DFG in both normoxic and hypoxic environment, suggesting autophagy as a major pathway of cell death under hypoxia.

Electron microscopy data indicate extensive presence of autophagosomes (a marker of autophagic cell death) after 72 h treatment of 5 mM 2-DFG under normoxia. Cell cycle experiments in U87 cells treated with 5 mM of 2-DFG show significant increase in G2/M phase with no significant increase in Sub G0/G1 phase indicating that the cell death is not mediated by apoptosis. In summary, these results demonstrate that 2-DFG is a potent inhibitor of glycolysis and inducer of autophagy and potentially promising novel antitumor agent for high grade gliomas and other cancers highly dependent on glycolysis.

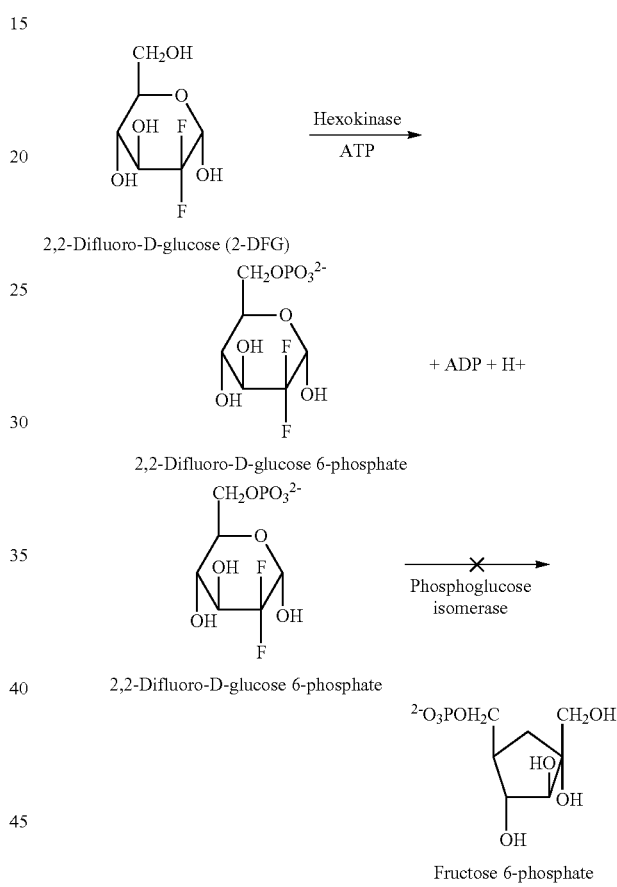

From the foregoing description, one skilled in the art can easily ascertain the essential characteristics of this invention, and without departing from the spirit and scope thereof, can make various changes and modifications of the invention to adapt it to various usages and conditions.

We claim:

1. A method of treating highly glycolytic brain tumors comprising administering to a subject in need thereof a therapeutically effective amount of 2-Deoxy-2,2-difluoro-D-arabino-hexopyranose.

* * * * *